(12) United States Patent
Saunders et al.

(10) Patent No.: US 7,439,249 B2
(45) Date of Patent: Oct. 21, 2008

(54) INHIBITORS OF PHOSPHATASES

(75) Inventors: Jeffrey O. Saunders, Acton, MA (US); Gregory F. Miknis, Broomfield, CO (US); Alexandre J. Buckmelter, Superior, CO (US); Kevin W. Hunt, Longmont, CO (US); James F. Blake, Longmont, CO (US); Guy P. A. Vigers, Boulder, CO (US); Xicheng Sun, Superior, CO (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 330 days.

(21) Appl. No.: 10/750,326

(22) Filed: Dec. 31, 2003

(65) Prior Publication Data

US 2004/0186116 A1    Sep. 23, 2004

Related U.S. Application Data

(60) Provisional application No. 60/437,567, filed on Dec. 31, 2002.

(51) Int. Cl.
*A61K 31/517* (2006.01)
*C07D 239/96* (2006.01)
*A61K 31/675* (2006.01)
*C07D 471/22* (2006.01)
*C07F 9/02* (2006.01)

(52) U.S. Cl. .................. 514/266.3; 514/81; 514/257; 514/266.2; 514/267; 544/244; 544/250; 544/284; 544/285

(58) Field of Classification Search .................. 514/81, 514/257, 266.2, 266.3, 267; 544/244, 250, 544/284, 285
See application file for complete search history.

(56) References Cited

U.S. PATENT DOCUMENTS 5,234,928 A * 8/1993 Fujimori et al. .......... 514/266.3

FOREIGN PATENT DOCUMENTS

| EP | 0 456 835 | 11/1991 |
|---|---|---|
| WO | WO 95/15963 | 6/1995 |
| WO | WO 98/18781 | 5/1998 |
| WO | WO 98/56770 | 12/1998 |

OTHER PUBLICATIONS

Malamas, et al., "Quinazolineacetic Acids and Related Analogues as Aldose Reductase Inhibitors", J. Med. Chem., vol. 34, No. 4, pp. 1492-1503 (1991).
Gordeev, et al., "A General and Efficient Solid Phase Synthesis of Quinazoline-2,4-diones.", Tetrahedron Letters, Vo. 38, No. 10, pp. 1729-1732 (1997).

* cited by examiner

*Primary Examiner*—James Wilson
*Assistant Examiner*—Tamthom N Truong
(74) *Attorney, Agent, or Firm*—Michael C. Badia

(57) ABSTRACT

The present invention relates to compounds that inhibit phosphatases, compositions thereof, and methods of using those compounds and compositions for treating diseases.

10 Claims, No Drawings

INHIBITORS OF PHOSPHATASES

CROSS-REFERENCE TO RELATED APPLICATIONS

The present application claims the benefit of U.S. provisional application 60/437,567, filed Dec. 31, 2002, the entire disclosure whereof is incorporated herein by reference.

TECHNICAL FIELD OF THE INVENTION

The present invention relates to compounds that inhibit phosphatases, compositions thereof, and methods of using those compounds and compositions for treating diseases.

BACKGROUND OF THE INVENTION

Many biologically important functions are regulated by the transfer of a phosphate group. Often, the active or inactive form of a compound is determined by the presence or absence of a phosphate group bound to that compound. Accordingly, many biological enzymes are involved in regulating this phosphate group transfer. For example, kinase enzymes catalyze transfer of a phosphate group from a nucleoside triphosphate to a protein receptor. In contrast, phosphatase enzymes remove a phosphate group from a substrate by hydrolysis.

SHP-2 (src homology 2-containing protein tyrosine phosphatase) is a 68 kDa phosphatase protein and is also known as SHPTP2, Syp, PTP1D and PTP2C. Lu et al., *Molecular Cell* (2001) 8, 759. The enzyme is expressed in the cytoplasm of every tissue. SHP-2 is an important signaling enzyme, and the biological functions of SHP-2 have been extensively reviewed. Feng, *Exp. Cell Res.* (1999) 253, 45; Neel and Tonks, *Curr. Opin. Cell Biol.* (1997) 9, 193; Tonks, *Adv. Pharmacol.* (1996) 36, 91. The enzyme is activated through interactions with a variety of ligands including growth factors, cytokine receptor tyrosine kinases, and adhesion molecules and is most notably recognized as a positive regulator of cell proliferation. SHP-2 also plays an important function in immune signaling. Huyer and Alexander, *Curr. Biol.* (1999) 9, R129; Cohen et al., *Cell* (1995) 80, 237. The SHP-2 enzyme is required for activation of the Ras-MAP kinase cascade, although its precise role in the pathway is unclear. Van Vactor et al., *Curr. Opin. Genet. Dev.* (1998) 8, 112. SHP-2 has recently been identified as an intracellular target of *Helicobacter pylori*. Higashi et al., *Science* (2002) 295, 683. Due to the critical role SHP-2 plays in various biological pathways, development of inhibitors against the enzyme would provide useful treatments for cancer and other autoimmune diseases.

Development of new chemical entities that modulate phosphatase enzymes such as SHP-2 would be an important advance and could lead to the development of novel treatments for diseases in which phosphatase enzymes play a critical role. The development of phosphatase modulators is an active area of research and has been extensively reviewed. Ripka, *Annual Rev. Med. Chem.* 2000, 35, Chapter 21 and references cited therein.

More recent work has focused on the development of new heterocyclic groups that can mimic a phosphate moiety, i.e. the development of phosphate isosteres. A successful phosphate isostere will ideally be both nonhydrolyzable and bioavailable. Successful phosphate mimicry will also depend on the shape and ionization state of the mimic. Examples of new heterocyclic groups designed to mimic a phosphate moiety include tetronic acid derivatives investigated against Cdc25b, Sodeoka et al., *J. Med. Chem.* (2001) 44(20), 3216, and the azoledinedione class of inhibitors that have been investigated against protein tyrosine phosphatase 1B (PTB1B). Malamas et al., *J. Med. Chem.* (2000) 43, 995. However, the efficacy of these mimics is still being investigated.

There is still a great need to develop potent modulators of phosphatase enzymes and other enzymes that are involved in regulating the transfer of a phosphate group.

SUMMARY OF THE INVENTION

The present invention relates to compounds of formula (I):

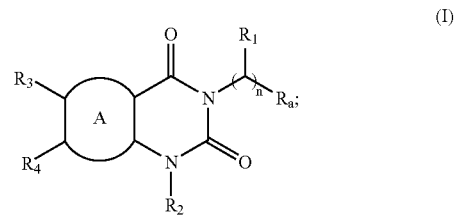

wherein:
ring A is an aryl or heteroaryl ring;
$R_a$ is —COOH, a salt or an ester thereof, or a bioisostere thereof;
n is 1-3;
$R_1$ is H, hydroxyaliphatic, aminoaliphatic, aliphatic-COOH, aliphatic—CONH$_2$, or arylaliphatic;
$R_2$ is aliphatic, arylaliphatic, cycloaliphatic-aliphatic, heteroarylaliphatic, or heterocyclylaliphatic; $R^3$ and $R^4$ are independently selected from $R^{11}$, $R^{12}$, $R^{14}$ or $R^{15}$;
wherein:
each $R^{11}$ is independently selected from 1,2-methylenedioxy, 1,2-ethylenedioxy, $R^6$ or $(CH_2)_m$—Y;
wherein m is 0, 1 or 2; and
Y is selected from halogen, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, COOH, COOR$^6$ or OR$^6$;
each $R^{12}$ is independently selected from ($C_1$-$C_6$)-straight or branched alkyl, or ($C_2$-$C_6$)-straight or branched alkenyl or alkynyl; and each $R^{12}$ optionally comprises up to 2 substituents, wherein:
the first of said substituents, if present, is selected from $R^{11}$, $R^{14}$ and $R^{15}$, and
the second of said substituents, if present, is $R^{11}$;
each $R^{14}$ is independently selected from OR$^{15}$, OC(O)R$^6$, OC(O)R$^{15}$, OC(O)OR$^6$, OC(O)OR$^{15}$, OC(O)N(R$^6$)$_2$, OP(O)(OR$^6$)$_2$, SR$^6$, SR$^{15}$, S(O)R$^6$, S(O)R$^{15}$, SO$_2$R$^6$, SO$_2$R$^{15}$, SO$_2$N(R$^6$)$_2$, SO$_2$NR$^{15}$R$^6$, SO$_3$R$^6$, C(O)R$^{15}$, C(O)OR$^{15}$, C(O)R$^6$, C(O)OR$^6$, NC(O)C(O)R$^6$, NC(O)C(O)R$^{15}$, NC(O)C(O)OR$^6$, NC(O)C(O)N(R$^6$)$_2$, C(O)N(R$^6$)$_2$, C(O)N(OR$^6$)R$^6$, C(O)N(OR$^6$)R$^{15}$, C(NOR$^6$)R$^6$, C(NOR$^6$)R$^{15}$, N(R$^6$)$_2$, NR$^6$C(O)R$^1$l, NR$^6$C(O)R$^6$, NR$^6$C(O)R$^{15}$, NR$^6$C(O)OR$^6$, NR$^6$C(O)OR$^{15}$, NR$^6$C(O)N(R$^6$)$_2$, NR$^6$C(O)NR$^{15}$R$^6$, NR$^6$SO$_2$R$^6$, NR$^6$SO$_2$R$^{15}$, NR$^6$SO$_2$N(R$^6$)$_2$, NR$^6$SO$_2$NR$^{15}$R$^6$, N(OR$^6$)R$^6$, N(OR$^6$)R$^{15}$, P(O)(OR$^6$)N(R$^6$)$_2$, and P(O)(OR$^6$)$_2$;
each $R^{15}$ is a cycloaliphatic, aryl, heterocyclyl, or heteroaromatic; and each $R^{15}$ optionally comprises up to 3 substituents, each of which, if present, is $R^{11}$;
each $R^6$ is independently selected from H, ($C_1$-$C_6$)-straight or branched alkyl, or ($C_2$-$C_6$) straight or branched alkenyl; and each $R^6$ optionally comprises a substituent that is $R^7$;

$R^7$ is a cycloaliphatic, aryl, heterocyclyl, or heteroaromatic; and each $R^7$ optionally comprises up to 2 substituents independently chosen from H, $(C_1-C_6)$-straight or branched alkyl, $(C_2-C_6)$ straight or branched alkenyl, 1,2-methylenedioxy, 1,2-ethylenedioxy, or $(CH_2)_p$-Z;
wherein p is 0, 1 or 2; and
Z is selected from halogen, CN, $NO_2$, $CF_3$, $OCF_3$, OH, $S(C_1-C_6)$-alkyl, $SO(C_1-C_6)$-alkyl, $SO_2(C_1-C_6)$-alkyl, $NH_2$, $NH(C_1-C_6)$-alkyl, $N((C_1-C_6)$-alkyl$)_2$, $N((C_1-C_6)$-alkyl$)R^8$, COOH, $C(O)O(C_1-C_6)$-alkyl or $O(C_1-C_6)$-alkyl; and
$R^8$ is an amino protecting group; provided that:
$R^3$ and $R^4$ are not simultaneously hydrogen;
when $R^3$ is H, then $R^4$ is not chloro; and
when $R^4$ is H, then $R^3$ is not —$SCH_3$ or —NH—$C(O)CH_3$.

The present invention also relates to compositions thereof, and methods of treating diseases using such compounds and compositions.

DETAILED DESCRIPTION OF THE INVENTION

The present invention relates to compounds of formula (I):

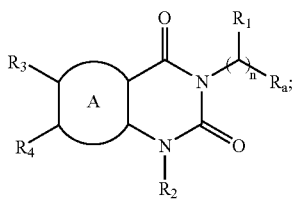

(I)

wherein:
ring A is an optionally substituted aryl or heteroaryl ring;
$R_a$ is —COOH;
n is 0-4;
$R_1$ is H, or an optionally substituted hydroxyaliphatic, aminoaliphatic, aliphatic, aliphatic—COOH, aliphatic-$CONH_2$, or arylaliphatic;
$R_2$ is an optionally substituted aliphatic, arylaliphatic, cycloaliphatic-aliphatic, heteroarylaliphatic, or heterocyclylaliphatic; $R^3$ and $R^4$ are independently selected from $R^{11}$, $R^{12}$, $R^{14}$ or $R^{15}$;
wherein:
each $R^{11}$ is independently selected from 1,2-methylenedioxy, 1,2-ethylenedioxy, $R^6$ or $(CH_2)_m$—Y;
wherein m is 0, 1 or 2; and
Y is selected from halogen, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;
each $R^{12}$ is independently selected from $(C_1-C_6)$-straight or branched alkyl, or $(C_2-C_6)$-straight or branched alkenyl or alkynyl; and each $R^{12}$ optionally comprises up to 2 substituents, wherein:
the first of said substituents, if present, is selected from $R^{11}$, $R^{14}$ and $R^{15}$, and
the second of said substituents, if present, is $R^{11}$;
each $R^{14}$ is independently selected from $OR^{15}$, $OC(O)R^6$, $OC(O)R^{15}$, $OC(O)OR^6$, $OC(O)OR^{15}$, $OC(O)N(R^6)_2$, $OP(O)(OR^6)_2$, $SR^6$, $SR^{15}$, $S(O)R^6$, $S(O)R^{15}$, $SO_2R^6$, $SO_2R^{15}$, $SO_2N(R^6)_2$, $SO_2NR^{15}R^6$, $SO_3R^6$, $C(O)R^{15}$, $C(O)OR^{15}$, $C(O)R^6$, $C(O)OR^6$, $NC(O)C(O)R^6$, $NC(O)$ $C(O)R^{15}$, $NC(O)C(O)OR^6$, $NC(O)C(O)N(R^6)_2$, $C(O)N$ $(R^6)_2$, $C(O)N(OR^6)R^6$, $C(O)N(OR^6)R^{15}$, $C(NOR^6)R^6$, $C(NOR^6)R^{15}$, $N(R^6)_2$, $NR^6C(O)R^{11}$, $NR^6C(O)R^6$, $NR^6C(O)R^{15}$, $NR^6C(O)OR^6$, $NR^6C(O)OR^{15}$, $NR^6C(O)$ $N(R^6)_2$, $NR^6C(O)NR^{15}R^6$, $NR^6SO_2R^6$, $NR^6SO_2R^{15}$, $NR^6SO_2N(R^6)_2$, $NR^6SO_2NR^{15}R^6$, $N(OR^6)R^6$, $N(OR^6)$ $R^{15}$, $P(O)(OR^6)N(R^6)_2$, and $P(O)(OR^6)_2$;
each $R^{15}$ is a cycloaliphatic, aryl, heterocyclyl, or heteroaromatic; and each $R^{15}$ optionally comprises up to 3 substituents, each of which, if present, is $R^{11}$;
each $R^6$ is independently selected from H, $(C_1-C_6)$-straight or branched alkyl, or $(C_2-C_6)$ straight or branched alkenyl; and each $R^6$ optionally comprises a substituent that is $R^7$;
$R^7$ is a cycloaliphatic, aryl, heterocyclyl, or heteroaromatic; and each $R^7$ optionally comprises up to 2 substituents independently chosen from H, $(C_1-C_6)$-straight or branched alkyl, $(C_2-C_6)$ straight or branched alkenyl, 1,2-methylenedioxy, 1,2-ethylenedioxy, or $(CH_2)_p$-Z;
wherein p is 0, 1 or 2; and
Z is selected from halogen, CN, $NO_2$, $CF_3$, $OCF_3$, OH, $S(C_1-C_6)$-alkyl, $SO(C_1-C_6)$-alkyl, $SO_2(C_1-C_6)$-alkyl, $NH_2$, $NH(C_1-C_6)$-alkyl, $N((C_1-C_6)$-alkyl$)_2$, $N((C_1-C_6)$-alkyl$)R^8$, COOH, $C(O)O(C_1-C_6)$-alkyl or $O(C_1-C_6)$-alkyl; and
$R^8$ is an amino protecting group; provided that:
$R^3$ and $R^4$ are not simultaneously hydrogen;
when $R^3$ is H, then $R^4$ is not chloro; and
when $R^4$ is H, then $R^3$ is not —$SCH_3$ or —NH—$C(O)CH_3$.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group", as used herein, means a straight-chain or branched, substituted or unsubstituted hydrocarbon chain that is completely saturated (alkyl) or is unsaturated (alkenyl or alkynyl). Unless otherwise specified, an aliphatic group has 1 to 12 carbon atoms. Preferably, an aliphatic group has 1-6 carbon atoms. Up to two —$CH_2$— in said aliphatic may be replaced with O, S, or —$NR_x$—.

The term "cycloaliphatic" means a 3-8 membered monocyclic hydrocarbon ring or a 8-12 membered bicyclic hydrocarbon ring that is completely saturated (e.g., cycloalkyl) or that contains one or more units of unsaturation (e.g., cycloalkenyl), but which is not aromatic, and has a single point of attachment to the rest of the molecule.

The term "heteroatom" unless otherwise specified means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "unsaturated", as used herein, means a double bond or a triple bond. Each such bond constitutes one unit of unsaturation.

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". Phenyl is an example of aryl.

The term "heterocycle", "heterocyclyl", "heterocycloaliphatic", or "heterocyclic" as used herein means non-aromatic, monocyclic, bicyclic or tricyclic ring systems having in total 5 to 14 ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems, wherein at least one ring in the system is aromatic, at least one ring in the system contains one or more heteroatoms. Unless otherwise specified, such ring systems have a total of 5 to 15 ring members, wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group include halogen, —R°, —OR°, —SR°, 1,2-methylene-dioxy, 1,2-ethylenedioxy, phenyl (Ph) optionally substituted with R°, —O(Ph) optionally substituted with R°, —CH$_2$(Ph) optionally substituted with R°, —CH$_2$CH$_2$(Ph),optionally substituted with R°, —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_q$NHC(O)R° wherein q is 0-2, and wherein each R° is independently selected from hydrogen, optionally substituted C$_1$-C$_6$ aliphatic, an unsubstituted 5-6 membered heteroaryl or heterocyclic ring, phenyl, —O(Ph), or —CH$_2$(Ph), or wherein two occurrences of R°, on the same substituent or different substituents, taken together, form a 5-8-membered heterocyclyl or heteroaryl ring having 1-3 heteroatoms independently selected from nitrogen, oxygen, or sulfur. Optional substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo C$_{1-4}$ aliphatic.

An aliphatic group or a non-aromatic heterocyclic ring may contain one or more substituents. Suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)2, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic).

Optional substituents on the nitrogen of a non-aromatic heterocyclic ring include —R$^+$, —N(R$^+$)$_2$, —C(O)R$^+$, —OR$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —CH$_2$CH$_2$(Ph), or an unsubstituted 5-6 membered heteroaryl or heterocyclic ring, or wherein two occurrences of R$^+$, on the same substituent or different substituents, taken together, form a 5-8-membered heterocyclyl or heteroaryl ring having 1-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic).

The term "alkylidene chain" refers to a straight or branched carbon chain that may be fully saturated or have one or more units of unsaturation and has two points of attachment to the rest of the molecule.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

According to a preferred embodiment, ring A is an optionally substituted 5 or 6 membered aryl or heteroaryl ring, wherein said heteroaryl ring contains up to 2 ring heteroatoms independently selected from O, S, or NR$^+$.

According to another preferred embodiment, ring A is phenyl.

According to another preferred embodiment, R$^1$ is hydrogen, —(CH$_2$)$_q$—X, wherein q is 1-4, and X is OH, NH$_2$, COOH or CONH$_2$, (C1-C6)-alkyl, or benzyl.

According to another preferred embodiment, R$^1$ is hydrogen, hydroxymethyl, methyl, —CH$_2$COOH, —CH$_2$CONH$_2$, aminobutyl, methyl, or isopentyl.

According to another preferred embodiment, R$^2$ is selected from butyl, isobutyl, methoxypropyl, cyclopentyl, cyclohexylmethyl, phenyl, trifluorophenyl, benzyl, fluorobenzyl, methylenedioxybenzyl, pyridylmethyl, furanylmethyl, tetrahydrofuranylmethyl, N-morpholinylmethyl, thienylmethyl, 2-oxo-pyrrolodinylpropyl, phenylethyl, chlorophenylethyl, methoxyphenylethyl, or dimethoxyphenylethyl.

According to another preferred embodiment, R$^2$ is selected from 2-furanylmethyl or methyl.

According to another preferred embodiment, R$^3$ and R$^4$ are independently selected from hydrogen, halo, acetamido, allyloxy, thiophenyl, sulfoxyalkyl, or sulfoxyphenyl.

The term "amino protecting group" refers to a suitable chemical group that may be attached to a nitrogen atom. The term "protected" refers to when the designated functional group is attached to a suitable chemical group (protecting group). Examples of suitable amino protecting groups and protecting groups are described in T. W. Greene and P. G. M.

Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); L. Paquette, ed. *Encyclopedia of Reagents for Organic Synthesis,* John Wiley and Sons (1995) and are exemplified in certain of the specific compounds used in this invention.

According to an alternate embodiment, the present invention provides compounds of formula (II):

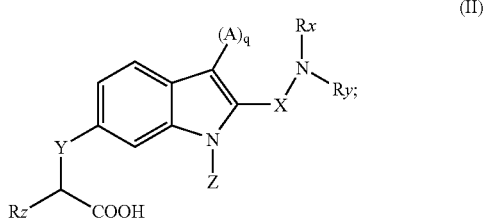

(II)

wherein:
X is —$(CH_2)_n$—, or —C(O)—;
n is 1-3;
Y is O, S, NH, or N(C1-C6 aliphatic);
Z is H or C1-C6 aliphatic;
Q is 0 or 1;

$A$, $R^x$, $R^y$, and $R^z$ are independently selected from $R^{11}$, $R^{12}$, $R^{14}$ or $R^{15}$;
  wherein:
  each $R^{11}$ is independently selected from 1,2-methylenedioxy, 1,2-ethylenedioxy, $R^6$ or $(CH_2)_m$—Y;
    wherein m is 0, 1 or 2; and
    Y is selected from halogen, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;
  each $R^{12}$ is independently selected from $(C_1-C_6)$-straight or branched alkyl, or $(C_2-C_6)$-straight or branched alkenyl or alkynyl; and each $R^{12}$ optionally comprises up to 2 substituents, wherein:
    the first of said substituents, if present, is selected from $R^{11}$, $R^{14}$ and $R^{15}$, and
    the second of said substituents, if present, is $R^{11}$;
  each $R^{14}$ is independently selected from $OR^{15}$, $OC(O)R^6$, $OC(O)R^{15}$, $OC(O)OR^6$, $OC(O)OR^{15}$, $OC(O)N(R^6)_2$, $OP(O)(OR^6)_2$, $SR^6$, $SR^{15}$, $S(O)R^6$, $S(O)R^{15}$, $SO_2R^6$, $SO_2R^{15}$, $SO_2N(R^6)_2$, $SO_2NR^{15}R^6$, $SO_3R^6$, $C(O)R^{15}$, $C(O)OR^{15}$, $C(O)R^6$, $C(O)OR^6$, $NC(O)C(O)R^6$, $NC(O)C(O)R^{15}$, $NC(O)C(O)OR^6$, $NC(O)C(O)N(R^6)_2$, $C(O)N(R^6)_2$, $C(O)N(OR^6)R^6$, $C(O)N(OR^6)R^{15}$, $C(NOR^6)R^6$, $C(NOR^6)R^{15}$, $N(R^6)_2$, $NR^6C(O)R^{11}$, $NR^6C(O)R^6$, $NR^6C(O)R^{15}$, $NR^6C(O)OR^6$, $NR^6C(O)OR^{15}$, $NR^6C(O)N(R^6)_2$, $NR^6C(O)NR^{15}R^6$, $NR^6SO_2R^6$, $NR^6SO_2R^{15}$, $NR^6SO_2N(R^6)_2$, $NR^6SO_2NR^{15}R^6$, $N(OR^6)R^6$, $N(OR^6)R^{15}$, $P(O)(OR^6)N(R^6)_2$, and $P(O)(OR^6)_2$;
  each $R^{15}$ is a cycloaliphatic, aryl, heterocyclyl, or heteroaromatic; and each $R^{15}$ optionally comprises up to 3 substituents, each of which, if present, is $R^{11}$;
  each $R^6$ is independently selected from H, $(C_1-C_6)$-straight or branched alkyl, or $(C_2-C_6)$ straight or branched alkenyl; and each $R^6$ optionally comprises a substituent that is $R^7$;
  $R^7$ is a cycloaliphatic, aryl, heterocyclyl, or heteroaromatic; and each $R^7$ optionally comprises up to 2 substituents independently chosen from H, $(C_1-C_6)$-straight or branched alkyl, $(C_2-C_6)$ straight or branched alkenyl, 1,2-methylenedioxy, 1,2-ethylenedioxy, or $(CH_2)_p$-Z;
    wherein p is 0, 1 or 2; and
    Z is selected from halogen, CN, $NO_2$, $CF_3$, $OCF_3$, OH, $S(C_1-C_6)$-alkyl, $SO(C_1-C_6)$-alkyl, $SO_2(C_1-C_6)$-alkyl, $NH_2$, $NH(C_1-C_6)$-alkyl, $N((C_1-C_6)$-alkyl$)_2$, $N((C_1-C_6)$-alkyl$)R^8$, COOH, $C(O)O(C_1-C_6)$-alkyl or $O(C_1-C_6)$-alkyl; and
  $R^8$ is an amino protecting group;
  or $R^x$ and $R^y$, taken together, form an optionally substituted heterocyclic ring having up to 3 substituents.

The scope of the present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention that, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment (e.g., the brain or lymphatic system) relative to the parent species.

The compounds of the present invention may be readily prepared using methods known in the art. One such synthetic route is illustrated below in Scheme 1. One of skill in the art will recognize that this synthetic route can be readily exploited for other embodiments of formula (I).

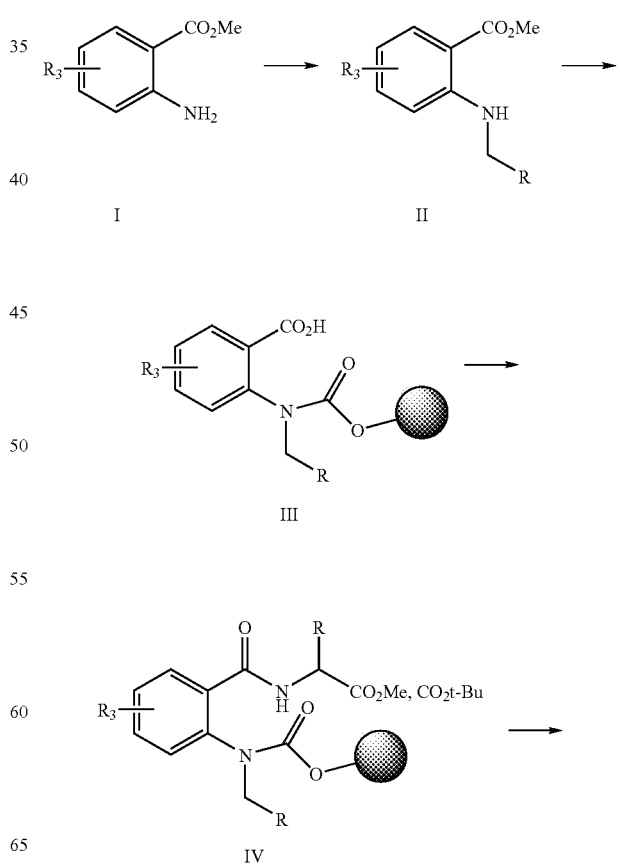

-continued

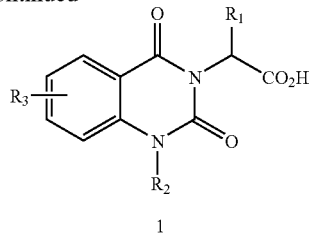

1

Preparation of compounds of formula (I) is carried out following the generalized procedures outlined in Scheme 1. The preparation of quinazolinediones involves 4 basic steps- i) reductive alkylation, ii) loading to resin, iii) peptide coupling and iv) cyclization and release from the resin.

Step 1. Reductive Alkylation of Anthranilic Acids

An anthranilic acid and aldehyde (4 eq) was dissolved in DCE at room temperature in the presence of acetic acid. After 15 minutes, sodium triacetoxyborohydride (4 eq) was added, and the solution stirred at room temperature (4-12 hrs. depending on the aldehyde used). The reaction was quenched with excess 1N NaOH and stirred for 20 minutes. The reaction was extracted several times with ethyl acetate, washed with brine, dried over sodium sulfate, filtered and concentrated. Purification was carried out via silica gel column chromatography using ethyl acetate/hexanes.

Saponification of the anthranilate esters was carried out by dissolving the ester in THF/MeOH and treated with 1 N lithium hydroxide at room temperature for 12 hrs. The reaction was concentrated to ⅓ the original volume, and poured into 10% NaOH. The solution was extracted with ether to remove unreacted material. The aqueous layer was collected and carefully acidified with 1N HCl. In most cases the anthranilic acids precipitated from solution and were collected by filtration. In the event that precipitation did not occur, the aqueous solution was diluted with brine solution and extracted several times with ethyl acetate. The organics were dried over sodium sulfate, filtered and concentrated to provide the desired anthranilic acids.

Step 2. Loading of Substituted Anthranilic Acids to Resin

CAUTION: The following procedure involves the use of phosgene and should only be carried out by an experienced technician in a well-vented chemical hood.

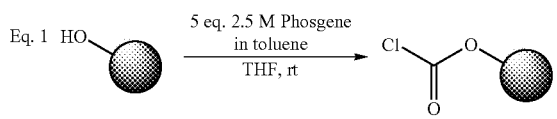

Preparation of Chloroformate Resin 10 grams of hydroxymethyl polystyrene (1.2 mmol/g loading) was weighed into a tared 250 ml peptide flask. The resin was washed with 100 ml dry THF and finally suspended in an additional 100 ml dry THF. To the resin suspension was added 25 ml (5.0 eq., 2.54 M) of a phosgene solution in toluene. The flask was sealed tightly and swirled on an orbital shaker for 2-3 hours. The peptide flasks were drained under positive pressure, collecting the mother liquor into a flask containing concentrated (20%) aqueous sodium hydroxide/methanol solution.

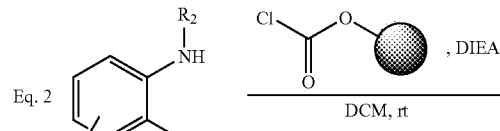

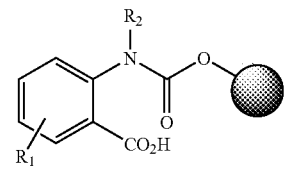

The chloroformate resin was subsequently washed 2×100 ml dry THF, 2×100 ml dry DCM using positive pressure to drain the vessel. A 100 ml DCM solution containing the anthranilic acid (3 eq) and DIEA (10 eq) was added quickly to the freshly prepared chloroformate resin and the flasks resealed and swirled on the orbital shaker for an additional 3½ hours. The resins were drained, washed and washed extensively. The resins were dried under high vacuum overnight. The approximate loading was determined by weight gain. Typical loadings of 0.7-0.9 mmol/g were routinely obtainable using this method.

Step 3. Coupling of Amino Acids to Anthranilic Acid Functionalized Resin 1-methyl-2-pyrrolidinone (NMP) solutions of HOBT (1M), HBTU (0.5 M), amino acid ester (1M) and Hunigs base (2M) were made freshly prior to carrying out the coupling reactions. The resin was suspended in NMP and a solution of HOBT (5 eq) was added followed by the addition of HBTU (5.0 eq). The reaction was sealed and shaken for 15 minutes. The vessel was unsealed and the reaction block placed on the Packard for addition of the remaining reagents. After 15 minutes, the solution of amino ester (4 eq) was added followed by the addition of diisopropyl ethylamine (5 eq). The reaction vessel was resealed and shaken for 18 hours at room temperature, after which the resin was subsequently washed extensively.

Step 4. Product Formation and Isolation

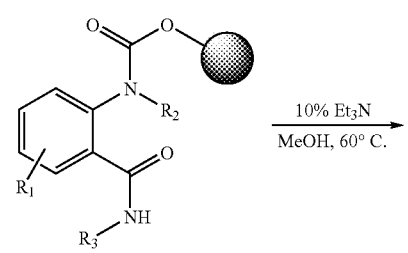

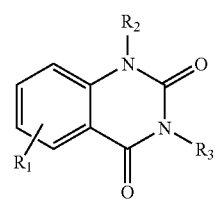

Cleavage of the products from the resins and isolation of the quinazoline-2,4-diones was carried out as follows. A solution of 10% triethylamine in methanol was added to the resin and the reaction vessel heated for 20 hours at 60-65° C. After the desired time, the reaction was cooled slightly and the mother liquor collected. The resin was washed 2× with methanol and the washings combined with the mother liquor. Concentration of the solution using a rotovaporator provided the desired quinazolinediones.

Subsequent removal of the butyl protecting groups was carried out by adding 1.5 mL of 95:3:2 TFA:water:triisopropyl silane to the crude quinazolinediones for 3 hrs at room temperature. The TFA solution was removed under vacuum and the compounds purified by C18 chromatography.

Preparation of compounds of formula (II) is carried out following the generalized procedures outlined in Scheme 2 below:

cylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{alkyl})_4$ salts. This invention also envisions the quaternization of any basic nitrogen-containing groups of the compounds disclosed herein. Water or oil-soluble or dispersible products may be obtained by such quaternization.

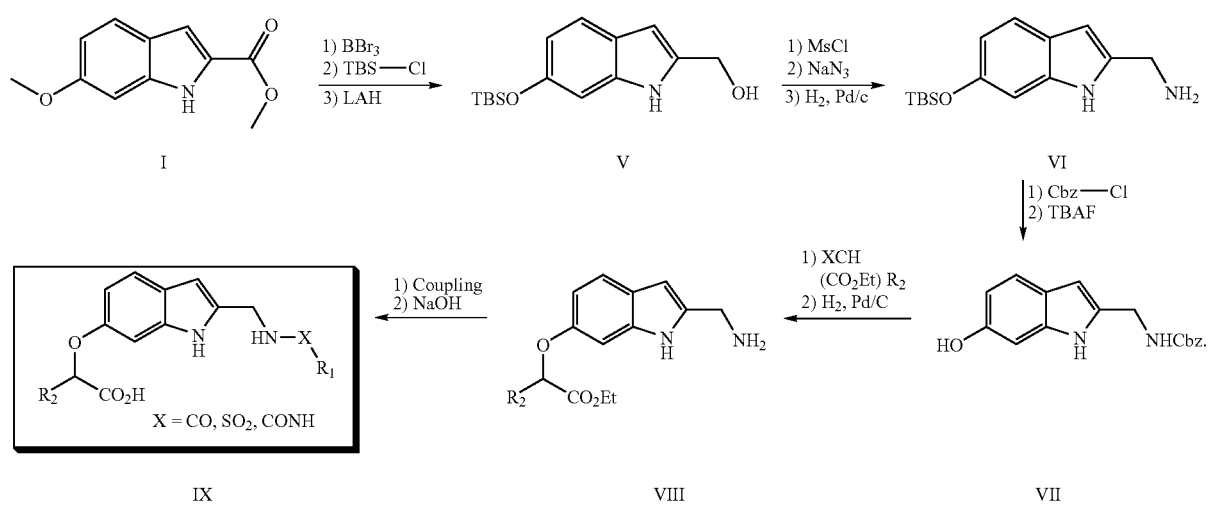

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, sali- The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

For example, chemotherapeutic agents or other anti-proliferative agents may be combined with the compounds of this invention to treat cancer and proliferative diseases. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents with which the compounds of this invention may be combined include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting SHP-2 phosphatase activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of SHP-2 phosphatase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of a disease selected from autoimmune diseases, proliferative diseases, angiogenic disorders, and cancers.

According to a preferred embodiment, the invention provides a method for treating or lessening the severity of a SHP-2-mediated disease or condition in a patient comprising the step of administering to said patient a composition according to the present invention.

The term "SHP-2-mediated disease," as used herein means any disease or other deleterious condition in which SHP-2 is known to play a role. Such conditions include, without limitation, autoimmune diseases, proliferative diseases, angiogenic disorders, and cancers.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma and HTLV-1-mediated tumorigenesis.

Angiogenic disorders that may be treated or prevented by the compounds of this invention include solid tumors, ocular neovasculization, infantile haemangiomas.

Cancers that may be treated or prevented by the compounds of this invention include, without limitation, colon, breast, stomach, and ovarian cancers.

In another embodiment, the methods of this invention that utilize compositions that do not contain an additional therapeutic agent, comprise the additional step of separately administering to said patient an additional therapeutic agent. When these additional therapeutic agents are administered separately, they may be administered to the patient prior to, sequentially with or following administration of the compositions of this invention.

The compounds of this invention or pharmaceutical compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by a suitable topcoat of fluorosilicone, polysaccarides, polyethylene glycol, phospholipids or combinations thereof to impart controlled-release characteristics in the composition.

Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXAMPLES

Example 1

Preparation of 2-(7-Acetylamino-1-furan-2-ylmethyl-2,4-dioxo-1,4-dihydro-2H-quinazolin-3-yl)-succinic acid (Compound 1)

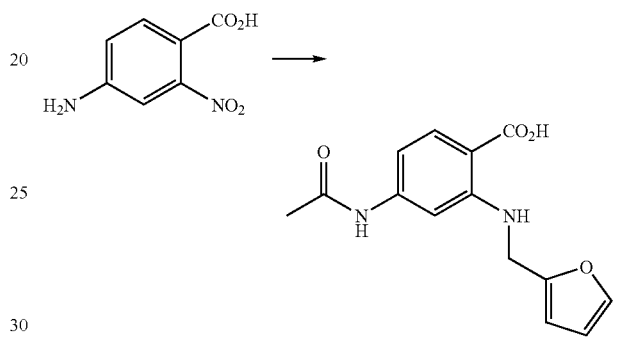

4-Acetylamino-2-[(furan-2-ylmethyl)-amino]-benzoic acid

The 4-amino-2-nitrobenzoic acid (3 g) was suspended in 20 ml 4:1 THF/MeOH, cooled to 0° C. TMS-diazomethane (5.6 g, 49 mmol, 3 eq, 2M in hex) was added dropwise and the solution stirred at room temperature for 2 hrs. The reaction was quenched with 1N acetic acid and the organics removed under vacuum. The aqueous layer poured into ethyl acetate, neutralized with sodium bicarbonate, dried over sodium sulfate, filtered and concentrated to a yellow oil. The ester was purified by flash column chromatography using 30% Acetone/hex. Isolated the nitroester as a bright yellow solid (92% yield).

The ester (1.0 g, 5.1 mmol) was dissolved in 20 ml DCM at room temperature. DIEA (0.98 g, 7.6mmol, 1.5 eq) was added followed by the addition of acetyl chloride (0.48 g, 6.1 mmol, 1.2 eq). Reaction was stirred at room temperature for 4 hrs. Reaction was poured into 1M HCl, dried over sodium sulfate, filtered and concentrated to a yellow oil/solid. The crude reaction was taken up in ~20 ml MeOH, saturated NH4Cl was added followed by the addition of excess Zn powder. Reaction was stirred at room temperature for 45 minutes when TLC showed complete reduction. The reaction was filtered to remove the Zn particulates, extracted with ethyl acetate. The aqueous layer was extracted 2×0 with ethyl aceate and the organics combined. Dried over sodium sulfate, filtered, and concentrated to a yellow film. The product was taken up in small amount of acetone and purified using 10-30% Acetone/ 2% MeOH/Hex as a gradient. Isolated the desired aniline compound as a light yellow solid (positive APCI, M+1=208.9)

Reductive amination was carried out by dissolving the anthranilate (2.3 g, 11 mmol, 1 eq), 2-furylaldehyde (3.2 g, 33 mmol, 3 eq) and 1 ml acetic acid in 50 ml DCE at room temperature. After 15 minutes sodium triacetoxyborohydride (9.4 g, 44 mmol, 4 eq) was added and the solution stirred at room temperature for 4 hrs. The reaction was quenched by addition of excess 1N NaOH. After stirring for 20 minutes, the suspension was extracted 3× with ethyl acetate. Washed the organics with brine, dried over sodium sulfate, filtered and concentrated to a brown oil. The product was isolated by flash column using 10-30% acetone/hex. The desired anilide was obtained a light yellow solid.

The ester was taken up in THF and 1N LiOH (1.5 eq) was added and stirred at 60° C. for 12 hrs. Reaction was cooled, concentrated to remove organics and diluted with water. The solution was washed with ether and the aqueous layer acidified with 1M HCl. A thick white precipitate formed and was collected by filtration to afford the desired compound.

NMR (DMSO-D6) δ=10.0 (s, 1H), 8.2 (bs, 1H), 7.66 (1H, D, J=8.6 Hz), 7.54 (1H, d, J=3.1 Hz), 7.18 (1H, D, J=2.3 Hz), 6.73 (1H, dd, J=1.5, 8.6 Hz), 6.36 (1H, dd, J=3.1, 2.3 Hz), 6.32 (1H, dd, J=1.5, 3.1 Hz), 4.3 (2H, s), 2.00 (3H, s).

MS m/e=273.1 (m−1) corresponds to C14H14N2O4, Mw=274.27.

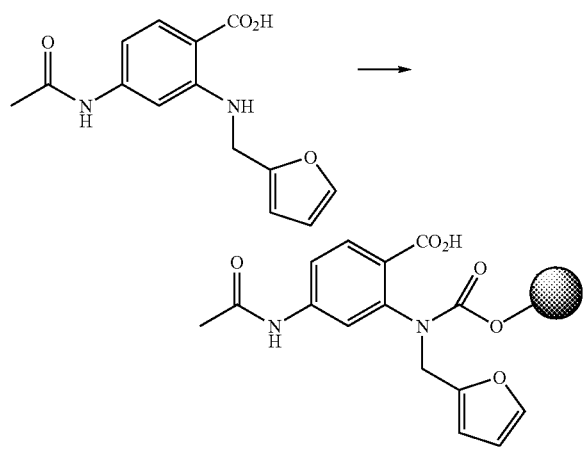

4 g of hydroxymethyl PS resin (1.2 mmol/g) was placed in a tared 100 ml peptide flask. The resin was washed 2× with dry THF and the resin suspended in a minimal amount of dry THF. A 2.5 M solution of phosgene in toluene (20ml) was added and the flask agitated for several hours. The reaction was filtered using postive nitrogen pressure, and the resin washed several times with DCM. A solution of 4-Acetylamino-2-[(furan-2-ylmethyl)-amino]-benzoic acid (compound 1, 3 eq) and DIEA (4 eq) in DCM was added to the resin and agitated for 3 hrs. The resin was filtered, washed several times with DMF, MeOH and DCM and dried under vacuum. Loading of the resin was calculated to be 0.9 mmol/g based on weight gain.

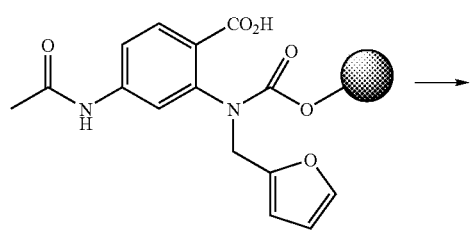

-continued

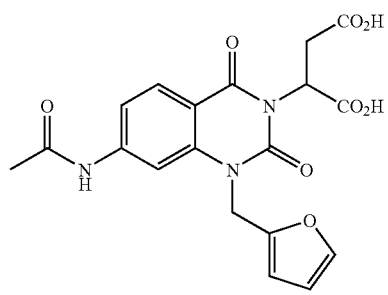

1

2-(7-Acetylamino-1-furan-2-ylmethyl-2,4-dioxo-1,4-dihydro-2H-quinazolin-3-yl)-succinic acid (Compound 1)

The resin (400 mg) was suspended in NMP and treated with HBTU (4 eq). HOBT (4 eq) for fifteen minutes before adding aspartic acid dit-butyl ester hydrochloride (3 eq.) and finally DIEA (4 eq). The reaction was agitated for 12 hours before filtering and washing extensively with NMP, DMF, MeOH. The resin was resuspended in 8 ml of 10% TEA/MeOH and heated to 60° C. for 18 hrs. The mother liquor was collected, and concentrated solutions to dryness. The crude quinazolinedione was deprotected using 50% TFA/DCM for 2 hrs. The reaction was concentrated under vacuum and the residue taken up in small amount of MeCN, and purified by C18 using MeCN/Water. Isolated a light-colored foam from azetrope with acetonitrile.

NMR (400 mHz, MeOH-D4) δ=8.19 (1H, d, J=2.3 Hz), 8.03 (1H, d, J=8.6 Hz), 7.42 (d, J=3.1 Hz), 7.29 (1H, dd, J=1.5, 8.6 Hz), 6.45 (1H, d, J=3.1 Hz), 6.34 (1H, dd, J=2.3, 3.1 Hz), 6.07 (1 H, m), 5.32 (2H, s), 3.40 (1H, dd, J=7.8 16.4 Hz), 2.81 (1H, dd, J=6.3, 16.4 Hz), 2.15 (3H, s). MS m/e=414 (m−1) corresponds to C19H17N3O8, Mw=415.35

Example 2

Preparation of 2-[6-Chloro-1-(5-methyl-furan-2-ylmethyl)-2,4-dioxo-1,4-dihydro-2H-quinazolin-3-yl]-succinic acid (Compound 2)

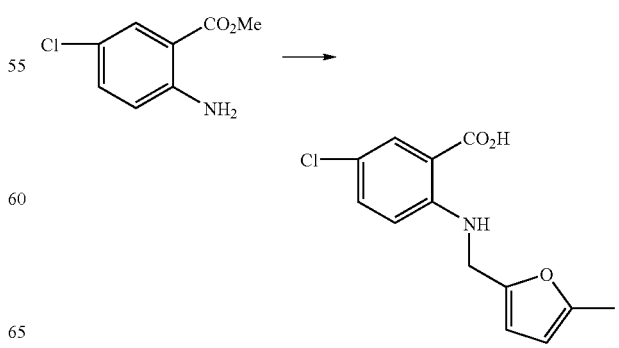

5-Chloro-2-[(5-methyl-furan-2-ylmethyl)-amino]-benzoic acid 911-71

Reductive amination of 5-chloro-2-amino-methylanthranilate carried out as described for compound 1 using 5-methyl furaldehyde in DCE for 4 hrs. After workup, the product was isolated by FC using 10-30% acetone/hexanes to afford a light yellow solid. The ester was subsequently taken up in THF and saponified using 1N at 60° C. for 12 hrs. The solution was cooled, acidified and the product collected as an off-white solid.

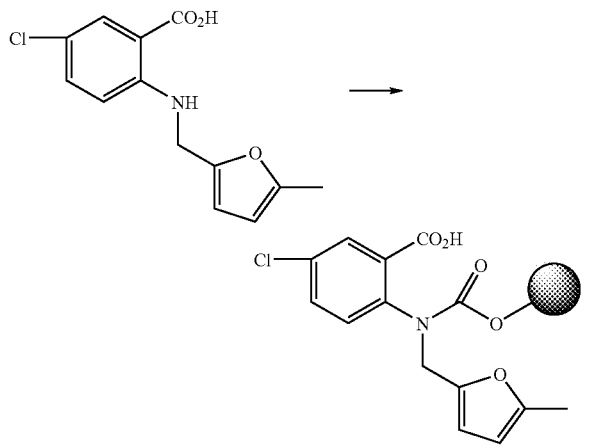

4.51 g of hydroxymethyl PS resin (1.2 mmol/g) was placed in a tared 100 ml peptide flask (tare=112.8423 g). The resin was washed 2× with THF and the resin suspended in a minimal amount of THF. A 2.5 M solution of phosgene in toluene (20 ml) was added and the flask agitated for several hours. Reaction was filtered under postive pressure, washed several times with DCM. A solution of the anthranilic acid and DIEA in DCM was added and the reaction agitated for 2 hrs. Reaction filtered, washed several times with DMF, MeOH and DCM. Dried under vacuum. Loading was calculated to be 0.96 mmol/g.

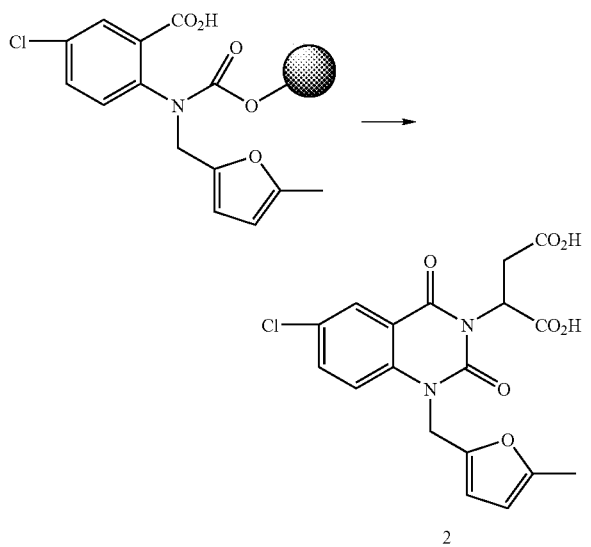

2-[6-Chloro-1-(5-methyl-furan-2-ylmethyl)-2,4-dioxo-1,4-dihydro-2H-quinazolin-3-yl]-succinic acid (Compound 2)

Dispensed 500 mg of resin into Quest 210 tubes. Added a solution of HOBT (2 ml, 1.0M in NMP, 4 eq) followed by the addition of HBTU in NMP (4 ml, 0.5 M, 4 eq). The resin was agitated for 15 minutes before adding an NMP solution of amine (4 ml, 5 eq) and DIEA (5 eq). The reaction was agitated for 18 hrs. The resins were filtered, washed extensively with DMF, MeOH and DCM, finally washing 3× with methanol.

The resin was taken up in 8 ml of 10% TEA/MeOH and heated to 60° C. for 20 hrs. The mother liquour was collected and concentrated to dryness. Compounds with protecting groups were deprotected using standard conditions and purified by FC using C18 and water/acetonitrile gradient to afford an off-white colored foam.

NMR (400 mHz, DMSO-D6) 67 =7.99 (1H, d, J=2.3 Hz), 7.84 (1H, dd, J=2.3, 8.6 Hz), 7.65 (1H, d, J=8.6 Hz), 6.25 (1H, D, J=3.1 Hz), 5.98 (1H, d, J=3.1 Hz), 5.85 (1H, dd, J=4.6, 8.6 Hz), 5.27 (2H, s), 3.31 (3H, s), 3.18 (1H, dd, J=8.6, 16.4 Hz), 2.69 (1H, dd, J=4.6 17.2 Hz). MS: m/e=405 (m−1) corresponds to C18H15ClN2O7 Mw=406.77

Example 3

Preparation of 2-(1-Furan-2-ylmethyl-6-methanesulfonyl-2,4-dioxo-1,4-dihydro-2H-quinazolin-3-yl)-succinic acid (Compound 3)

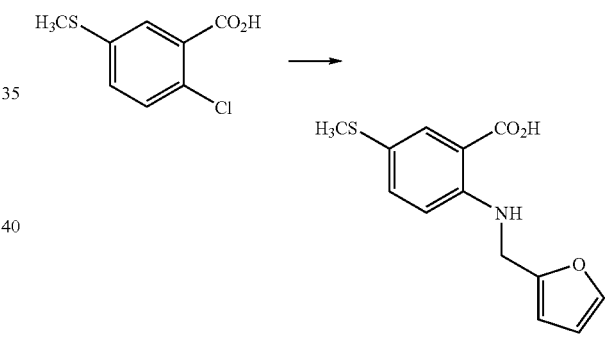

2-[(Furan-2-ylmethyl)-amino]-5-methylsulfanyl-benzoic acid

2-Chloro-5-(methylthio)benzoic acid (15.5 g, 76.5 mmol) was dissolved in DMF (20 mL). Potassium carbonate (10.6 g, 76.7 mmol) was added, and the solution stirred for 5 min (until effervescence subsides). Furfurylamine (8.8 mL, 99 mmol) was then added followed by copper(I) bromide (1 g, 7 mmol). The reaction was heated to 150° C. overnight in a sealed tube, then (while still hot) poured into 10% NH$_4$OH (300 mL). The mixture was acidified to pH 4-5 (by pH paper) with glacial AcOH and the crude product was collected by filtration. The collected solids were then dissolved in 1N NaOH and the insoluble black particulates were filtered off. The filtrate was then acidified with 6N AcOH and the product (an olive solid, 11.64 g, 58%) was collected by filtration and dried under high vacuum for 2 days to remove most of the residual water. $^1$H NMR (400 MHz, DMSO) δ 7.70 (d, J=2.3 Hz, 1H), 7.60 (d, J=1.6 Hz, 1H), 7.39 (dd, J=8.6, 2.3 Hz, 1H), 6.86 (d, J=8.6 Hz, 1H), 6.40 (dd, J=3.1, 1.6 Hz, 1H), 6.33 (d, J=3.1 Hz, 1H), 4.46 (s, 2H), 2.37 (s, 3H). MS (LR-APCI) calcd. for $C_{13}H_{14}NO_3S$ (M+H) 264.07; found 263.9.

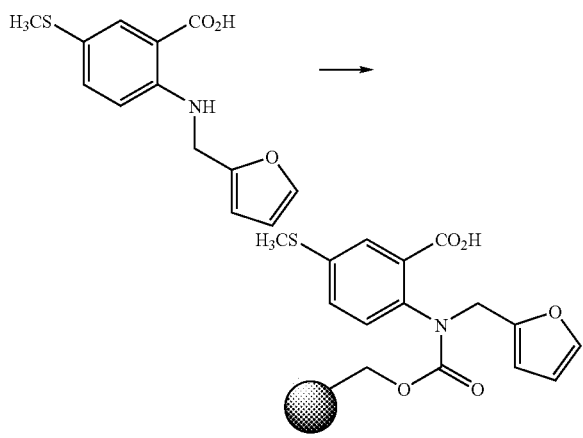

Hydroxymethyl polystyrene (HM-PS) resin (5.988 g, 1.29 mmol/g) was taken up in THF and phosgene (15 mL of a ~2.5 M solution in toluene) was added. The reaction was shaken for 3 h, and the phosgene solution was then drained (use caution)) and washed successively with DCM (4×). A solution of 2-[(Furan-2-ylmethyl)-amino]-5-methylsulfanyl-benzoic acid (3.07 g, 1.5 equiv) in DCM was then added to the resin along with DIEA (6.6 mL, 5 equiv) and the reaction shaken for another 3 h. The resin was then rinsed successively with DCM (3×), MeOH (3×), DCM (3×), MeOH (3×) and Et₂O (2×) and dried under high vacuum. Yield of resin=8.811 g (estimated loading by weight gain substitution=1.10 mmol/g).

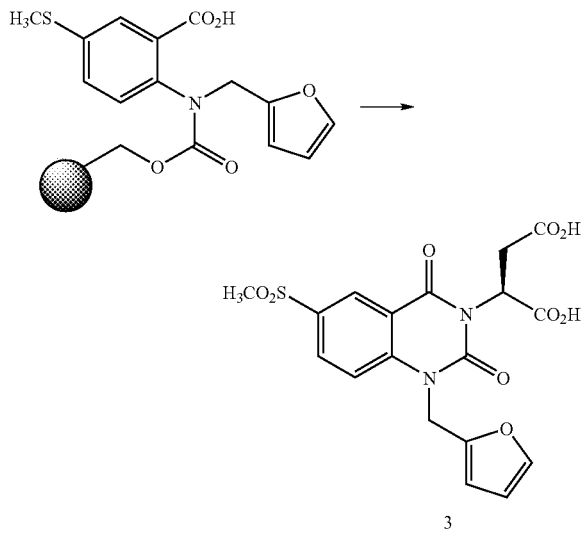

2-(1-Furan-2-ylmethyl-6-methanesulfonyl-2,4-dioxo-1,4-dihydro-2H-quinazolin-3-yl)-succinic acid (Compound 3)

The PS resin was taken up in NMP and HOBT H₂O (4 equiv in NMP) and HBTU (4 equiv in NMP) were added. After shaking for ~5 min, L-aspartic acid ☐,☐-di-t-butyl ester hydrochloride (4 equiv in NMP) and DIEA (5 equiv) were added to the mixture. After shaking overnight, the solution was drained, and the resin washed successively with NMP (2×), DCM (3×), and MeOH (3×) and dried under high vacuum. The resin was heated to 60° C. overnight in 10% Et₃N/MeOH solution in order to affect cyclative cleavage of the compound from resin. The crude product was then purified by chromatography (SiO₂, R$_f$=0.29 in 20% EtOAc/hexanes). The 6-methylsulfanyl-quinazoline-2,4-dione was then taken up in CHCl₃ and cooled in an ice bath. MCPBA (~77%, ~2 equiv) was then added and the reaction monitored by TLC for conversion to the sulfone. Once satisfactory conversion is achieved, 1N NaOH was added and the layers separated. The organic layer was dried (MgSO₄) and the sulfone was purified by chromatography (SiO₂, R$_f$=0.39 in 60% EtOAc/hexanes). Treatment of the 6-methanesulfonyl-quinazoline-2,4-dione with TFA/DCM (1:1) overnight afforded the crude final product, which was purified by reverse phase C18 chromatography. ¹H NMR (400 MHz, CD₃CN) δ 8.60 (s, 1H), 8.21 (d, J=9.4 Hz, 1H), 7.74 (d, J=8.6 Hz, 1H), 7.48 (s, 1H), 6.46-6.41 (m, 2H), 6.02 (t, LJ=7.0 Hz, 1H), 5.38 (s, 2H), 3.35 (dd, J=17.2, 7.8 Hz, 1H), 3.12 (s, 3H), 2.80 (dd, J=17.2, 5.5 Hz, 1 H). MS (LR-APCI) calcd. for C₁₈H₁₅N₂O₉S (M−H) 435.05; found 435.0.

The following additional derivatives were prepared using the same chemical transformation as previously described.

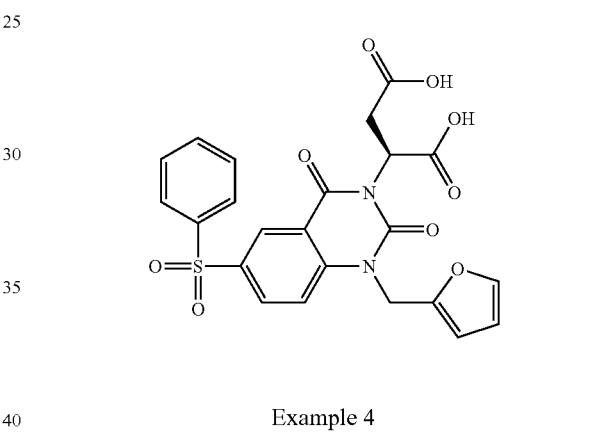

Example 4

2-(6-Benzenesulfonyl-1-furan-2-ylmethyl-2,4-dioxo-1,4-dihydro-2H-quinazolin-3-yl)-succinic acid ¹H NMR (400 MHz, DMSO-d₆) δ 7.83 (s, 1H), 7.41 (d, J=9.4 Hz, 1H), 7.16 (d, J=7.8 Hz, 2H), 6.96 (d, J=8.6 Hz, 1H), 6.83 (t, J=7.8 Hz, 1H), 6.77 (t, J=7.3 Hz, 2H), 6.60 (s, 1H), 5.57 (d, J=3.2 Hz, 1H), 5.52 (app s, 1H), 5.24 (t, J=7.4 Hz, 1H), 4.57 (s, 2H), 2.56 (dd, J=18.0, 7.8 Hz, 1H), 2.03 (dd, J=16.4, 6.3 Hz, 1 H). MS (LR-APCI) calcd. for C₂₃H₁₇N₂O₉S (M−H) 497.07; found 496.9.

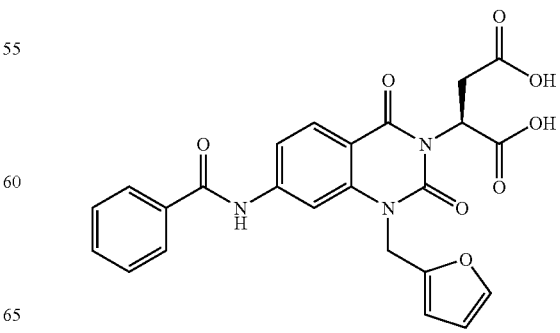

Example 5

2-(7-Benzoylamino-1-furan-2-ylmethyl-2,4-dioxo-1,4-dihydro-2H-quinazolin-3-yl)-succinic acid $^1$H NMR (400 MHz, CD$_3$CN) δ 9.13 (s, 1H), 8.27 (d, J=1.6 Hz, 1H), 8.12 (d, J=8.6 Hz, 1H), 7.98 (d, J=7.0 Hz, 1H), 7.65 (app t, J=7.4 Hz, 1H), 7.57 (app t, J=7.4 Hz, 4H), 7.48 (d, J=2.3 Hz, 1H), 6.52 (d, J=3.1 Hz, 1H), 6.41 (app t, J=2.6 Hz, 1H), 6.04 (dd, J=8.2, 5.1 Hz, 1H), 5.33 (d, J=2.3 Hz, 2H), 3.34 (dd, J=16.8, 8.2 Hz, 1H), 2.78 (dd, J=16.4, 5.5 Hz, 1 H). MS (LR-APCI) calcd. for C$_{24}$H$_{18}$N$_3$O$_8$ (M−H) 476.11; found 476.0.

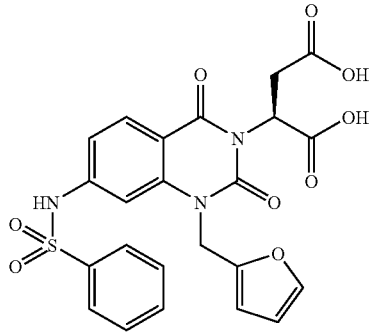

Example 6

2-(7-Benzenesulfonylamino-1-furan-2-ylmethyl-2,4-dioxo-1,4-dihydro-2H-quinazolin-3-yl)-succinic acid $^1$H NMR (400 MHz, CD$_3$CN) δ 8.58 (s, 1H), 7.98 (d, J=8.6 Hz, 1H), 7.83 (d, J=8.6 Hz, 2H), 7.64 (app t, J=7.0 Hz, 1H), 7.53 (app t, J=7.8 Hz, 2H), 7.48 (s, 1H), 7.30 (s, 1H), 7.01 (d, J=8.6 Hz, 1H), 6.45-6.43 (m, 1H), 6.38 (d, J=3.1 Hz, 1H), 5.98 (dd, J=7.8, 5.5 Hz, 1H), 5.23 (d, J=3.9 Hz, 2H), 3.29 (dd, J=16.4, 7.8 Hz, 1H), 2.73 (dd, J=17.2, 5.5 Hz, 1 H). MS (LR-APCI) calcd. for C$_{23}$H$_{18}$N$_3$O$_9$S (M−H) 512.08; found 512.1.

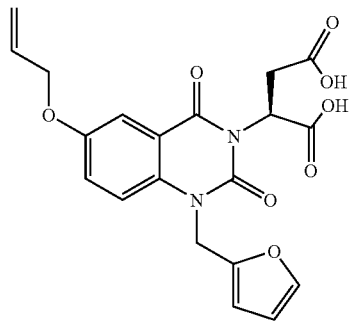

Example 7

2-(6-Allyloxy-1-furan-2-ylmethyl-2,4-dioxo-1,4-dihydro-2H-quinazolin-3-yl)-succinic acid 1H NMR (400 MHz, CD$_3$CN) δ 7.61 (d, J=3.1 Hz, 1H), 7.48-7.43 (m, 2H), 7.35 (dd, J=8.6, 3.1 Hz, 1H), 6.40-6.35 (m, 2H), 6.12-6.01 (m, 2H), 5.45-5.27 (m, 4H), 4.64 (d, J=4.7 Hz, 2H), 3.32 (dd, J=16.4, 7.8 Hz, 1H), 2.78 (dd, J=16.4, 5.5 Hz, 1H). MS (LR-APCI) calcd. for C$_{20}$H$_{17}$N$_2$O$_8$ (M−H) 413.10; found 413.0.

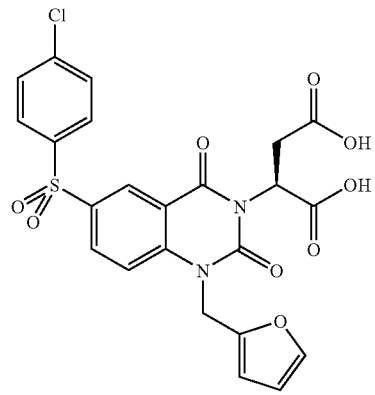

Example 8

2-[6-(4-Chloro-benzenesulfonyl)-1-furan-2-ylmethyl-2,4-dioxo-1,4-dihydro-2H-quinazolin-3-yl]-succinic acid $^1$H NMR (400 MHz, CD$_3$CN) δ 8.59 (d, J=2.3 Hz, 1H), 8.18 (dd, J=9.4, 2.3 Hz, 1H), 7.97 (d, J=8.6 Hz, 2H), 7.69 (d, J=8.6 Hz, 2H), 7.60 (d, J=8.6 Hz, 2H), 7.43 (s, 1H), 6.40-6.37 (m, 2H), 6.00 (dd, J=7.8, 5.5 Hz, 1H), 5.32 (d, J=3.1 Hz, 2H), 3.31 (dd, J=17.2, 7.8 Hz, 1H), 2.77 (dd, J=17.2, 5.5 Hz, 1H). MS (LR-APCI) calcd. for C$_{23}$H$_{16}$ClN$_2$O$_9$S (M−H) 531.03; found 530.8.

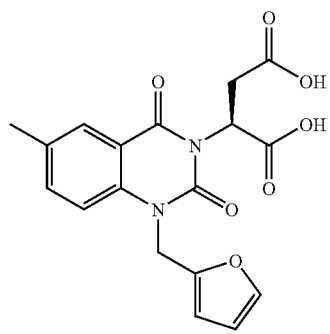

Example 9

2-(1-Furan-2-ylmethyl-6-methyl-2,4-dioxo-1,4-dihydro-2H-quinazolin-3-yl)-succinic acid $^1$H NMR (400 MHz, DMSO-d$_6$) δ 7.87 (s, 1H), 7.63-7.59 (m, 2H), 7.53 (d, J=8.6 Hz, 1H), 6.41 (s, 2H), 5.90 (dd, J=8.6, 4.7 Hz, 1H), 5.34 (s, 2H), 3.21 (dd, J=16.4, 8.6 Hz, 1H), 2.70 (dd, J=16.4, 4.7 Hz, 1H), 2.37 (s, 3H). MS (LR-APCI) calcd. for C$_{18}$H$_{15}$N$_2$O$_7$ (M−H) 371.09; found 371.0.

J=8.6 Hz, 2H), 7.55 (d, I=8.6 Hz, 2H), 7.43 (s, 1H), 6.39 (s, 2H), 6.02 (dd, J=7.8, 5.5 Hz, 1H), 5.32 (t, J=3.1 Hz, 2H), 3.32 (dd, J=17.2, 7.8 Hz, 1H), 2.78 (dd, J=17.2, 5.5 Hz, 1H). MS (LR-APCI) calcd. for C$_{23}$H$_{16}$ClN$_2$O$_8$S (M−H) 515.03; found 515.3.

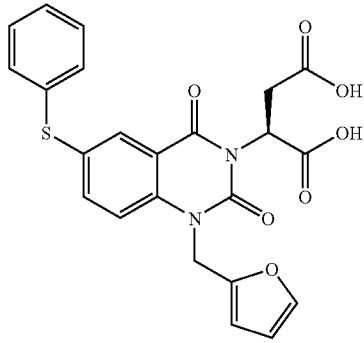

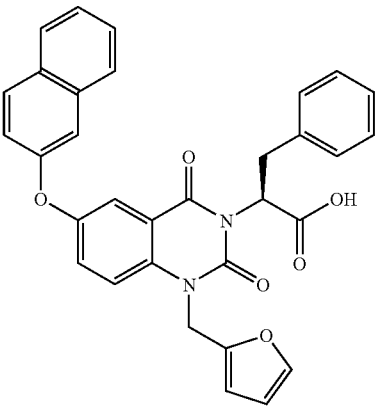

Example 10

2-(1-Furan-2-ylmethyl-2,4-dioxo-6-phenylsulfanyl-1,4-dihydro-2H-quinazolin-3-yl)-succinic acid $^1$H NMR (400 MHz, CD$_3$CN) δ 8.01 (s, 1H), 7.67 (dd, J=8.6, 2.3 Hz, 1H), 7.49 (d, J=8.6 Hz, 1H), 7.44 (s, 1H), 7.42-7.37 (m, 5H), 6.38 (s, 2H), 5.99 (dd, J=7.8, 5.5 Hz, 1H), 5.30 (s, 2H), 3.30 (dd, J=17.2, 8.6 Hz, 1H), 2.75 (dd, J=17.2, 5.5 Hz, 1H). MS (LR-APCI) calcd. for C$_{23}$H$_{17}$N$_2$O$_7$S (M−H) 465.08; found 465.0.

Example 12

2-(6-Chloro-1-furan-2-ylmethyl-2,4-dioxo-1,4-dihydro-2H-quinazolin-3-yl)-succinic acid $^1$H NMR (Acetone-D6) δ=8.07 (1H, d, J=2.3 Hz), 7.89 (1H, dd, J=1.5, 8.6 Hz), 7.69 (1H, d, J=8.6 Hz), 7.5 (1H, s), 6.44 (1H, d, J=3.1 Hz), 6.39 (1H, d, J=2.3 Hz), 6.15 (1H, dd, J=4.6, 8.6 Hz), 5.43 (2H, s), 3.49 (1H, dd, J=8.6, 16.4 Hz), 2.87 (1H, dd, J=4.6, 16.4 Hz) MS (negative APCI) m/e=391 (m−1) corresponds to C17H13ClN2O7 Mol. Wt.: 392.75

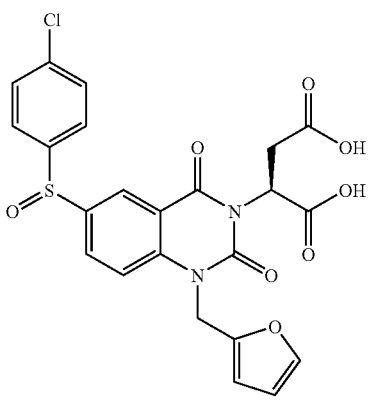

Example 11

2-[6-(4-Chloro-benzenesulfinyl)-1-furan-2-ylmethyl-2,4-dioxo-1,4-dihydro-2H-quinazolin-3-yl]-succinic acid $^1$H NMR (400 MHz, CD$_3$CN) δ 8.41 (d, J=2.3 Hz, 1H), 7.94 (dd, J=10.2, 1.6 Hz, 1H), 7.71 (d, J=7.8 Hz, 2H), 7.65 (d,

Example 13

2-[1-Furan-2-ylmethyl-6-(naphthalen-2-yloxy)-2,4-dioxo-1,4-dihydro-2H-quinazolin-3-yl]-3-phenyl-propionic acid $^1$H NMR (400 MHz, CD$_3$CN) δ 7.95 (d, J=8.6 Hz, 1H), 7.92 (d, J=7.8 Hz, 1H), 7.78 (d, J=7.8 Hz, 1H), 7.59 (s, 1H), 7.54-7.41 (m, 5H), 7.38 (s, 1H), 7.27 (d, J=7.8 Hz, 1H), 7.13 (s, 5H), 6.40 (s, 1H), 6.25 (s, 1H), 5.89 (dd, J=11.0, 5.5 Hz, 1

H), 5.27 (s, 2H), 3.50 (dd, J=14.1, 5.5 Hz, 1H), 3.42 (dd, J=14.1, 11.0, 1H). MS (LR-APCI) calcd. for $C_{32}H_{23}N_2O_6$ (M−H) 531.16; found 531.0.

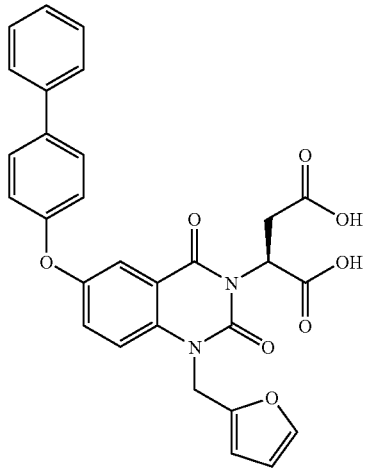

Example 14

2-[6-(Biphenyl-4-yloxy)-1-furan-2-ylmethyl-2,4-dioxo-1,4-dihydro-2H-quinazolin-3-yl]-succinic acid $^1$H NMR (400 MHz, CD$_3$CN) δ0 7.70-7.64 (m, 5H), 7.57 (d, J=8.6 Hz, 1H), 7.50-7.44 (m, 4H), 7.37 (t, J=7.4 Hz, 1H), 7.13 (d, J=8.6 Hz, 2H), 6.40 (s, 2H), 6.01 (dd, J=7.8, 5.5 Hz, 1H), 5.33 (s, 2H), 3.32 (dd, J=16.4, 7.8 Hz, 1H), 2.78 (dd, J=16.4, 5.5 Hz, 1H). MS (LR-APCI) calcd. for $C_{29}H_{21}N_2O_8$ (M−H) 525.13; found 525.8.

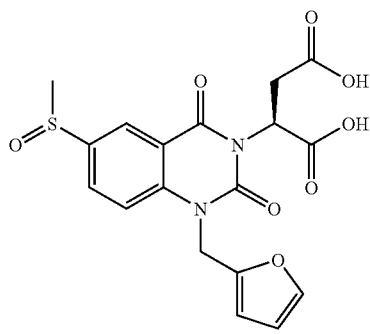

Example 15

2-(1-Furan-2-ylmethyl-6-methanesulfinyl-2,4-dioxo-1,4-dihydro-2H-quinazolin-3-yl)-succinic acid $^1$H NMR (400 MHz, CD$_3$CN) δ 8.38 (d, J=2.3 Hz, 1H), 8.00 (dd, J=8.6, 2.3 Hz, 1H), 7.72 (d, J=8.6 Hz, 1H), 7.46 (d, J=2.3 Hz, 1H), 6.44-6.40 (m, 2H), 6.04 (dd, J=7.8, 5.5 Hz, 1H), 5.37 (s, 2H), 3.33 (dd, J=16.4, 7.8 Hz, 1H), 2.81 (dd, J=16.4, 5.5 Hz, 1H), 2.74 (s, 3H). MS (LR-APCI) calcd. for $C_{18}H_{15}N_2O_8S$ (M−H) 419.05; found 418.9.

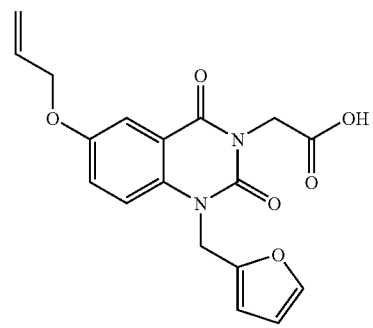

Example 16

(6-Allyloxy-1-furan-2-ylmethyl-2,4-dioxo-1,4-dihydro-2H-quinazolin-3-yl)-acetic acid $^1$H NMR (400 MHz, CD$_3$CN) δ 7.62 (d, J=3.1 Hz, 1H), 7.49 (d, J=9.4 Hz, 1H), 7.45 (s, 1H), 7.36 (dd, J=9.4, 3.1 Hz, 1H), 6.40-6.37 (m, 2H), 6.14-6.04 (m, 1H), 5.44 (d, J=18.0 Hz, 1H), 5.33 (s, 2H), 5.30 (d, J=11.7 Hz, 1H), 4.75 (s, 2H), 4.65 (d, J=4.7 Hz, 2H). MS (LR-APCI) calcd. for $C_{18}H_{15}N_2O_6$ (M−H) 355.09; found 355.1

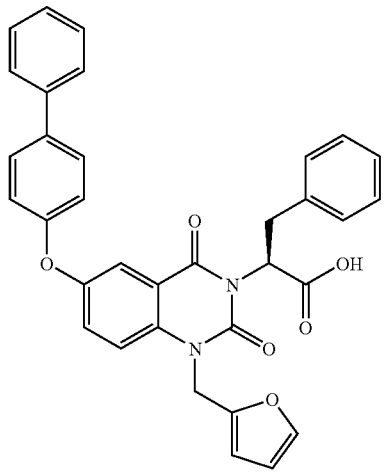

Example 17

2-[6-(Biphenyl-4-yloxy)-1-furan-2-ylmethyl-2,4-dioxo-1,4-dihydro-2H-quinazolin-3-yl]-3-phenyl-propionic acid $^1$H NMR (400 MHz, CD$_3$CN δ 7.38 (app t, J=9.0 Hz, 4H), 7.28 (s, 1H), 7.22-7.07 (m, 6H), 6.86-6.81 (m, 7H), 6.12 (s, 1H), 5.96 (s, 1H), 5.61 (dd, J=11.0, 5.5 Hz, 1H), 4.99 (s, 2H), 3.23 (dd, J=13.7, 5.5 Hz, 1H), 3.15 (dd, J=13.7, 11.0 Hz, 1H). MS (LR-APCI) calcd. for $C_{34}H_{25}N_2O_6$ (M−H) 557.17; found 557.0.

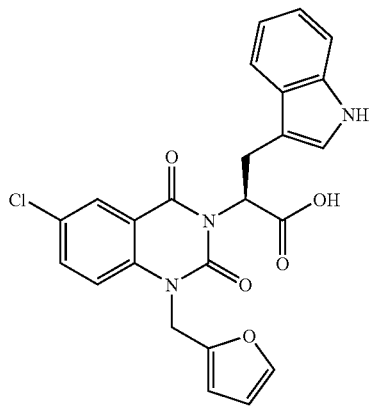

Example 18

2-(6-Chloro-1-furan-2-ylmethyl-2,4-dioxo-1,4-dihydro-2H-quinazolin-3-yl)-3-(1H-indol-3-yl)-propionic acid $^1$H NMR (MeOH-D4) δ=10.08 (1H, bs), 7.88 (1H, bs), 7.60 (1H, dd, J=3.1, 9.4 Hz), 7.41 (2H, d, J=9.4 Hz), 7.36 (1H, d, J=7.8 Hz), 7.19 (1H, d, J=8.6 Hz), 6.95 (1H, d, J=7.8 Hz), 6.92 (2H, s), 6.75 (1H, trp, J=7.8 Hz), 6.31 (1H, bs), 5.89 (1H, dd, J=5.4, 10.9 Hz), 5.21 (2H, s), 3.73 (1H, dd, J=10.9, 14.8 Hz), 3.63 (1H, dd, J=5.4, 15.6 Hz)

MS (negative APCI) m/e=461.9 (m−1) corresponds to C24H18ClN3O5 Mol. Wt.: 463.87

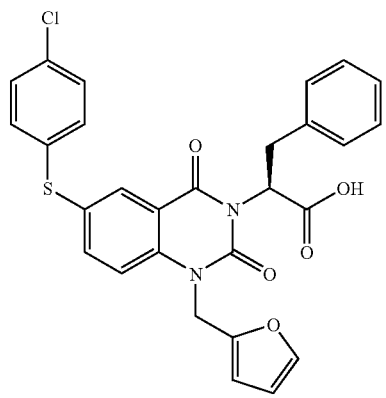

Example 19

2-[6-(4-Chloro-phenylsulfanyl)-1-furan-2-ylmethyl-2,4-dioxo-1,4-dihydro-2H-quinazolin-3-yl]-3-phenyl-propionic acid $^1$H NMR (400 MHz, DMSO-d$_6$) δ 7.82 (s, 1H), 7.72 (dd, J=8.6, 2.3 Hz, 1H), 7.63 (d, J=7.8 Hz, 2H), 7.45 (d, J=8.6 Hz, 2H), 7.33 (d, J=8.6 Hz, 2H), 7.14-7.07 (m, 5H), 6.42 (s, 1H), 6.30 (s, 1H), 5.76 (dd, J=10.2, 6.3 Hz, 1H), 5.30 (s, 2H), 3.49-3.30 (m, 2H). MS (LR-APCI) calcd. for C$_{28}$H$_{20}$ClN$_2$O$_5$S (M−H) 531.08; found 531.0.

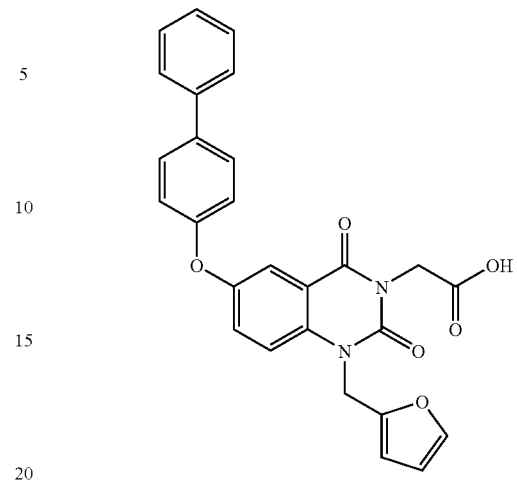

Example 20

[6-(Biphenyl-4-yloxy)-1-furan-2-ylmethyl-2,4-dioxo-1,4-dihydro-2H-quinazolin-3-yl]-acetic acid $^1$H NMR (400 MHz, DMSO-d$_6$) δ 7.76-7.60 (m, 7H), 7.56 (d, J=3.1 Hz, 1H), 7.46 (t, J=7.4 Hz, 2H), 7.36 (t, J=7.4 Hz, 1H), 7.16 (d, J=8.6 Hz, 2H), 6.48 (d, LJ=3.1 Hz, 1H), 6.44-6.42 (m, 1H), 5.40 (s, 2H), 4.62 (s, 2H). MS (LR-APCI) calcd. for C$_{27}$H$_{19}$N$_2$O$_6$ (M−H) 467.12; found 466.9.

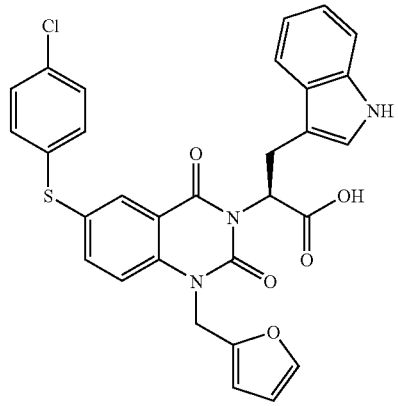

Example 21

2-[6-(4-Chloro-phenylsulfanyl)-1-furan-2-ylmethyl-2,4-dioxo-1,4-dihydro-2H-quinazolin-3-yl]-3-(1H-indol-3-yl)-propionic acid $^1$H NMR (400 MHz, CD$_3$CN) δ 8.87 (s, 1H), 7.80 (s, 1H), 7.51 (dd, J=8.6, 2.3 Hz, 1H), 7.34-7.30 (m, 2H), 7.29-7.25 (m, 3H), 7.20-7.16 (m, 3H), 6.92 (t, J=7.0 Hz, 1H), 6.85 (d, J=2.3 Hz, 1H), 6.73 (t, J=7.8 Hz, 1H), 6.27 (s,1H), 5.93 (s, 1H), 5.77 (dd, J=9.4, 7.0 Hz, 1H), 5.10 (app d, J=7.8 Hz, 2H), 3.52-3.47 (m, 2H). MS (LR-APCI) calcd. for C$_{30}$H$_{21}$ClN$_3$O$_5$S (M−H) 570.09; found 569.9.

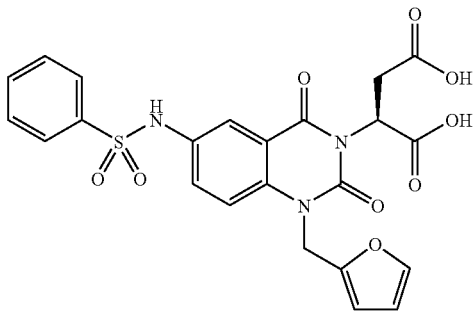

Example 21

2-(6-Benzenesulfonylamino-1-furan-2-ylmethyl-2,4-dioxo-1,4-dihydro-2H-quinazolin-3-yl)-succinic acid $^1$H NMR (400 MHz, DMSO-d$_6$) δ 10.57 (s, 1 H), 7.75-7.47 (m, 9 H), 6.40-6.37 (m, 2 H), 5.82-5.72 (m, 1 H), 5.24 (s, 2 H), 3.22-3.14 (m, 1 H), 2.65-2.56 (m, 1 H). MS (LR-APCI) calcd. for C$_{23}$H$_{18}$N$_3$O$_9$S (M−H) 512.08; found 512.0.

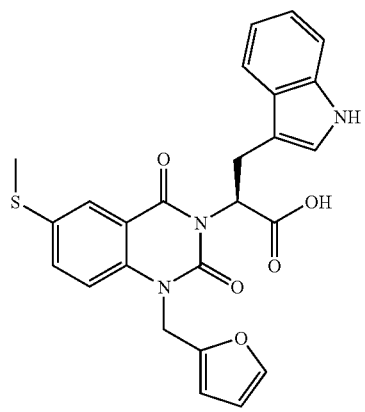

Example 22

2-(1-Furan-2-ylmethyl-6-methylsulfanyl-2,4-dioxo-1,4-dihydro-2H-quinazolin-3-yl)-3-(1H-indol-3-yl)-propionic acid $^1$H NMR (400 MHz, CD$_3$CN) δ 8.86 (s, 1H), 7.71 (s, 1H), 7.46 (dd, J=8.6, 2.3 Hz, 1H), 7.36 (d, J=7.8 Hz, 1H), 7.31 (s, 1H), 7.22 (d, J=8.6 Hz, 1H), 7.19 (d, J=7.8 Hz, 1H), 6.92 (t, J=7.0 Hz, 1H), 6.85 (s, 1H), 6.77 (t, J=7.4 Hz, 1H), 6.25 (s, 1H), 5.90 (s, 1H), 5.81 (dd, J=9.4, 6.3 Hz, 1H), 5.10 (app d, J=7.0 Hz, 2H), 3.54-3.49 (m, 2H), 2.38 (s, 3H). MS (LR-APCI) calcd. for C$_{25}$H$_{20}$N$_3$O$_5$S (M−H) 474.11; found 473.9.

Example 23

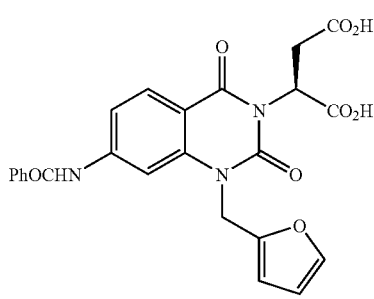

2-(7-Benzoylamino-1-furan-2-ylmethyl-2,4-dioxo-1,4-dihydro-2H-quinazolin-3-yl)-succinic acid $^1$H NMR (400 MHz, CD$_3$CN) δ 9.13 (s, 1H), 8.27 (d, J;=1.6 Hz, 1H), 8.12 (d, J=8.6 Hz, 1H), 7.98 (d, J=7.0 Hz, 1H), 7.65 (app t, J=7.4 Hz, 1H), 7.57 (app t, J=7.4 Hz, 4H), 7.48 (d, J=2.3 Hz, 1H), 6.52 (d, J=3.1 Hz, 1H), 6.41 (app t, J=2.6 Hz, 1H), 6.04 (dd, J=8.2, 5.1 Hz, 1H), 5.33 (d, J=2.3 Hz, 2H), 3.34 (dd, J=16.8, 8.2 Hz, 1H), 2.78 (dd, J=16.4, 5.5 Hz, 1 H). MS (LR-APCI) calcd. for C$_{24}$H$_{18}$N$_3$O$_8$ (M−H) 476.11; found 476.0.

Example 24

2-[2-(Benzenesulfonylamino-methyl)-1H-indol-6-yloxy]-malonic acid

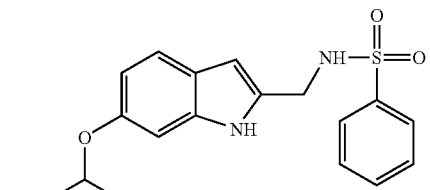

Step A: 6-(tert-Butyl-dimethyl-silanyloxy)-1H-indole-2-carboxylic acid

6-Hydroxy-1H-indole-2-carboxylic acid (5.40 g, 30.48 mmol) is dissolved in THF (100 ml) and imidazole (10.38, 152.4 mmol) is added. The mixture is stirred for 5 minutes, TBDMS-Cl (13.78 g, 91.44 mmol) is added. The reaction is stirred at room temperature for 1 hour. The mixture is filtered into water (200 ml). The solid is washed with THF (50 ml). The filtrate is concentrated to remove THF. The product is extracted with ethyl acetate (100 ml) three times. The organic is dried (MgSO$_4$), filtered, and concentrated to provide 6-(tert-Butyl-dimethyl-silanyloxy)-1H-indole-2-carboxylic acid (8.0 g, 90% yield). $^1$H NMR (400 MHz, DMSO-d6): δ 12.73 (s, 1H) , 11.43 (s, 1H), 7.49 (d, 1H), 7.00 (s, 1H), 6.84 (s, 1H), 6.63 (m, 1H), 0.97 (s, 9H), 0.20 (s, 6H).

Step B: [6-(tert-Butyl-dimethyl-silanyloxy)-1H-indol-2-yl]-methanol

1M LAH in THF (103 ml) is cooled to 0° C. A solution of 6-(tert-Butyl-dimethyl-silanyloxy)-1H-indole-2-carboxylic acid (6.0 g, 20.60 mmol) in THF (30 ml) is added slowly. The reaction is stirred at room temperature for two days, quenched with water (10 ml), 1N NaOH (10 ml) and water (20 ml). To the mixture MgSO$_4$ is added. The mixture is filtered, washed with 10% methanol in ethyl acetate (200 ml). The filtrate is concentrated to oil. The crude is purified by column chromatography (20% ethyl acetate in hexanes) to provide [6-(tert-Butyl-dimethyl-silanyloxy)-1H-indol-2-yl]-methanol (2.30 g, 40% yield). $^1$H NMR (400 MHz, DMSO-d6): δ 10.72 (s,1H), 7.28 (d, 1H), 6.76 (s,1H), 6.50 (m,1H), 6.16 (s,1H), 5.13 (t, 1H), 4.52 (d, 2H), 0.96 (s, 9H), 0.17 (s, 6H).

Step C: 2-Azidomethyl-6-(tert-butyl-dimethyl-silanyloxy)-1H-indole

[6-(tert-Butyl-dimethyl-silanyloxy)-1H-indol-2-yl]-methanol (2.0 g, 7.21 mmol) is dissolved in DMF (950 ml), cooled to 0° C. TEA (2.01 ml, 14.42 mmol) and MsCl (0.83 g, 7.21 mmol) are added. The mixture is stirred at room temperature for 1 hour. NaN$_3$ (2.34 g, 34 mmol) is added. The reaction is stirred at room temperature for 1 hour and then 80° C. overnight. The mixture is cooled to room temperature, concentrated. The residue is purified by column chromatography (10% ethyl acetate in hexanes) to give 2-Azidomethyl-6-(tert-butyl-dimethyl-silanyloxy)-1H-indole (1.40 g, 64%). $^1$H NMR (400 MHz, DMSO-d6): δ 11.08 (s, 1H), 7.38 (d, 1H), 6.80 (s, 1H), 6.58 (m, 1H), 6.40 (s, 1H), 4.53 (d, 2H), 0.96 (s, 9H), 0.17 (s, 6H).

Step D: [6-(tert-Butyl-dimethyl-silanyloxy)-1H-indol-2-yl]-methylamine

2-Azidomethyl-6-(tert-butyl-dimethyl-silanyloxy)-1H-indole (0.70 g, 2.31 mmol), is dissolved in ethanol (10 ml). 100 mg of 10% Pd/C is added. The mixture is hydrogenated at 40 psi of hydrogen overnight to give [6-(tert-Butyl-dimethyl-silanyloxy)-1H-indol-2-yl]-methylamine.

Step E: [6-(tert-Butyl-dimethyl-silanyloxy)-1H-indol-2 ylmethyl]-carbamic acid benzyl ester

[6-(tert-Butyl-dimethyl-silanyloxy)-1H-indol-2-yl]-methylamine (0.70 g, 1.01 mmol) is dissolved in DCM (10 ml), cooled to 0° C. DIEA (0.35 ml, 2.02 mmol) and Cbz-Cl (0.17 g, 1.01 mmol) are added. The mixture is stirred for 1 hour at room temperature. The reaction mixture is concentrated and the residue is purified by column chromatography (10% ethyl acetate in hexanes) to provide [6-(tert-Butyl-dimethyl-silanyloxy)-1H-indol-2-ylmethyl]-carbamic acid benzyl ester.

Step F: (6-Hydroxy-1H-indol-2-ylmethyl)-carbamic acid benzyl ester

[6-(tert-Butyl-dimethyl-silanyloxy)-1H-indol-2-ylmethyl]-carbamic acid benzyl ester (0.80 g, 1.95 mmol) is dissolved in THF (2 ml). Cooled to −78° C. 1 M TBAF solution in THF (3.90 ml) is added. The reaction mixture is concentrated and the residue is purified by column chromatography (30% ethyl acetate in hexanes) to obtain (6-Hydroxy-1H-indol-2-ylmethyl)-carbamic acid benzyl ester.

Step G: 2-(2-Aminomethyl-1H-indol-6-yloxy)-malonic acid diethyl ester (6-Hydroxy-1H-indol-2-ylmethyl)-carbamic acid benzyl ester was dissolved in 10 ml acetone, Cs$_2$CO$_3$ and diethyl chloromalonate were added. The reaction is stirred overnight. HPLC and TLC indicated the reaction is done. The mixture was diluted with ethyl acetate and filtered through silica gel plug. The filtrate is concentrated and redissolved in ethanol, hydrogenated for 3 hours at 40 psi of hydrogen. The mixture is filtered, washed with ethyl acetate. The filtrate is concentrated to give 2-(2-Aminomethyl-1H-indol-6-yloxy)-malonic acid diethyl ester.

Step H: 2-[2-(Benzenesulfonylamino-methyl)-1H-indol-6-yloxy]-malonic acid diethyl ester 2-(2-Aminomethyl-1H-indol-6-yloxy)-malonic acid diethyl ester (80 mg, 0.2 5 mmol) is dissolved in DCM (2 ml). DIEA (87 □l, 0.50 mmol) is added. To the solution, benzenesulfonyl chloride (44 mg, 0.25 mmol) is added. The reaction is stirred at room temperature for two hours. The reaction mixture is concentrated and the residue is purified by chromatography (30% ethyl acetate in hexanes) to give the title compound.

Step 1: 2-[2-(Benzenesulfonylamino-methyl)-1H-indol-6-yloxy]-malonic acid

2-[2-(Benzenesulfonylamino-methyl)-1H-indol-6-yloxy]-malonic acid diethyl is dissolved in ethanol (3 ml). 1M NaOH (2 ml) is added. The mixture is stirred for 1 hour. The mixture was acidified with 1M HCl to pH=2 and purified by C18 column chromatography (15% atetonitrile in water). $^1$H NMR (400 MHz, DMSO-d6): δ 10.76 (s,1H), 8.04 (t,1H), 7.82 (d, 2H), 7.54-7.64 (m, 3H), 7.23 (d, 1H), 6.72 (s, 1H), 6.57 (d, 1H), 6.06 (s, 1H), 5.07 (s, 1H), 4.01 (d, 2H); MS (ES-) m/z 403 (M−1).

The following compounds can be prepared using similar chemistry to that which is described above:

Example 24

2-[2-(Phenylmethanesulfonylamino-methyl)-1H-indol-6-yloxy]-malonic acid

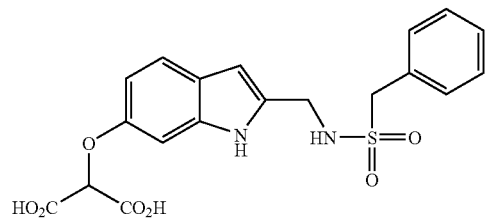

$^1$H NMR (400 MHz, DMSO-d6): δ 10.89 (s, 1H), 7.60 (t, 1H), 7.30-7.38 (m, 6H), 6.88 (s, 1H), 6.67 (m, 1H), 6.27 (s, 1H), 5.25 (s, 1H), 4.31 (s, 2H); 4.18 (d, 2H); MS (ES-) m/z 417 (M−1).

Example 25

2-{2-[(4-Acetylamino-benzenesulfonylamino)-methyl]-1H-indol-6-yloxy}-malonic acid

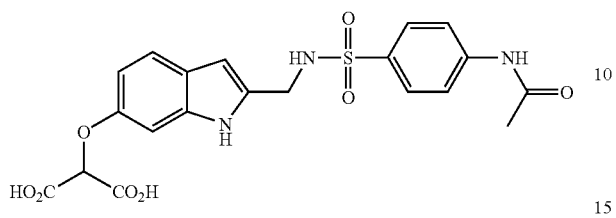

$^{1}$H NMR (400 MHz, DMSO-d6): δ 10.71 (s, 1H), 10.26 (s, 1H), 7.85 (t, 1H), 7.68 (m, 4H), 7.20 (d, 1H), 7.00 (d, 1H), 6.69 (s, 1H), 6.55 (d, 1H), 6.05 (s, 1H), 5.04 (s, 1H), 3.96 (d, 2H); 2.03 (s, 3H); MS (ES-) m/z 460 (M−1).

Example 26

2-{2-[(Biphenyl-4-sulfonylamino)-methyl]-1H-indol-6-yloxy}-malonic acid

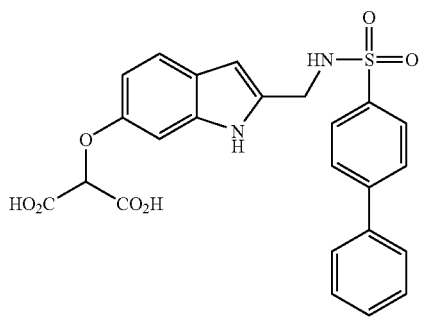

$^{1}$H NMR (400 MHz, DMSO-d6): δ 10.91 (s, 1H), 8.14 (t, 1H), 7.44-7.91 (m, 9H), 7.30 (d, 1H), 6.84 (s, 1H), 6.64 (m, 1H), 6.14 (s, 1H), 5.22 (s, 1H), 4.10 (d, 2H); MS (ES-) m/z 479 (M−1).

Example 27

2-{2-([(1-Acetyl-piperidine-4-carbonyl)-amino]-methyl}-1H-indol-6-yloxy)-malonic acid

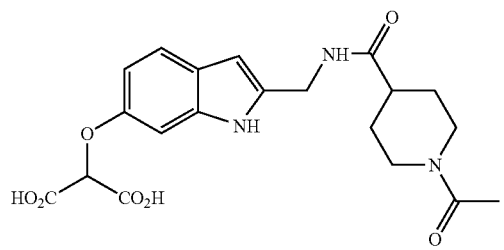

$^{1}$H NMR (400 MHz, DMSO-d6): δ 10.61 (s, 1H), 8.20 (t, 1H), 7.21 (d, 1H), 6.66 (s, 1H), 6.52 (m, 1H), 4.94 (s, 1H), 4.29 (m, 2H), 3.78 (d, 1H), 3.40 (m, 1H), 2.97 (m, 1H), 2.34-2.53 (m, 2H), 1.95 (s, 3H), 1.69 (m, 2H), 1.50 (m, 1H), 1.35 (m, 1H); MS (ES-) m/z 416 (M−1).

Example 28

2-[2-(Methanesulfonylamino-methyl]-1H-indol-6-yloxyl-malonic acid

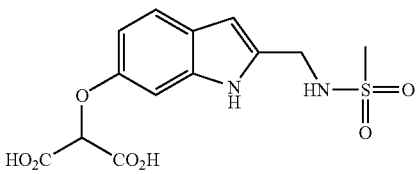

$^{1}$H NMR (400 MHz, DMSO-d6): δ 10.88 (s, 1H), 7.60 (t, 1H), 7.30-7.38 (m, 6H), 6.97 (s, 2H), 6.80 (s, 1H), 6.65 (m, 1H), 6.28 (s, 1H), 5.39 (s, 1H), 4.24 (d, 2H); 2.85 (s, 3H); MS (ES-) m/z 341 (M−1).

Example 29

2-{2-[(3,5-Bis-trifluoromethyl-phenylmethanesulfonylamino)-methyl]-1H-indol-6-yloxy}-malonic acid

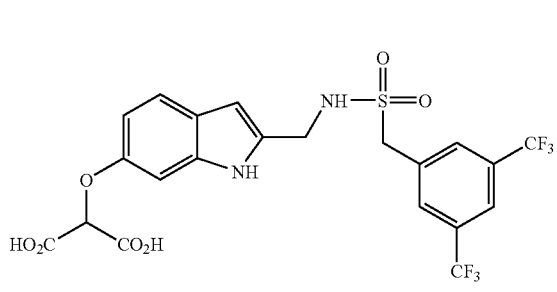

1H NMR (400 MHz, DMSO-d6): δ 10.65 (s, 1H), 8.17 (t, 1H), 8.15 (s, 1H), 8.05 (s, 1H), 7.91 (s, 1H), 7.16 (d, 1H), 6.58 (s, 1H), 6.49 (m, 1H), 6.05 (s,1H), 5.04 (m, 2H), 4.84 (s,1H), 4.19 (s, 2H); MS (ES-) m/z 553 (M−1).

Example 30

2-{2-[(3,5-Dichloro-phenylmethanesulfonylamino)-methyl]-1H-indol-6-yloxy}-malonic acid

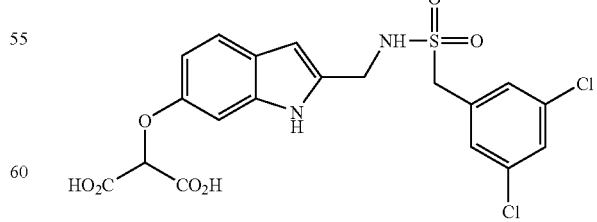

$^{1}$H NMR (400 MHz, DMSO-d6): δ 10.75 (s,1H), 7.66 (t, 1H), 7.15-7.52 (m, 4H), 6.93 (d, 1H), 6.56 (m, 1H), 6.27 (s, 1H), 5.25 (s, 1H), 4.31 (s, 2H); 4.18 (d, 2H); MS (ES-) m/z 485 (M−1).

Example 31

2-{2-[(2,2-Diphenyl-ethanesulfonylamino)-methyl]-1H-indol-6-yloxy}-malonic acid

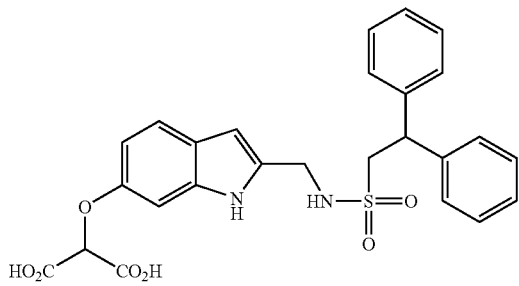

$^1$H NMR (400 MHz, DMSO-d6): δ 10.77 (s, 1H), 7.47 (t, 1H), 7.12-7.32 (m, 11H), 6.76 (s, 1H), 6.62 (m,1H), 6.17 (s,1H), 5.07 (s, 1H), 4.46 (m, 1H); 4.14 (d, 2H), 3.82 (d, 2H), MS (ES-) m/z 507 (M−1).

Example 32

2-{2-[(4'-Methyl-biphenyl-4-sulfonylamino)-methyl]-1H-indol-6-yloxy}-malonic acid

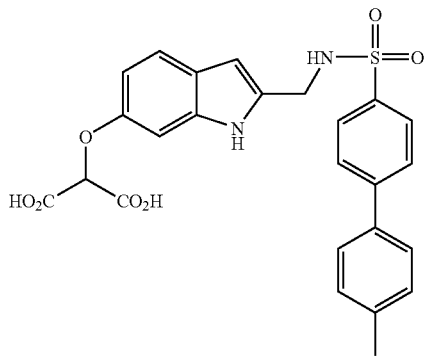

$^1$H NMR (400 MHz, DMSO-d6): δ 10.88 (s, 1H), 8.11 (t, 1H), 7.82-7.88 (m, 4H), 7.62 (d, 2H), 7.32 (d, 2H), 7.29 (d, 1H), 6.82 (s, 1H), 6.64 (m, 1H), 6.14 (s, 1H), 5.19 (s, 1H), 4.08 (d, 2H); 2.40 (s, 3H), MS (ES-) m/z 493 (M−1).

Example 33

2-{2-[(4'-Chloro-biphenyl-4-sulfonylamino)-methyl]-1H-indol-6-yloxy}-malonic acid

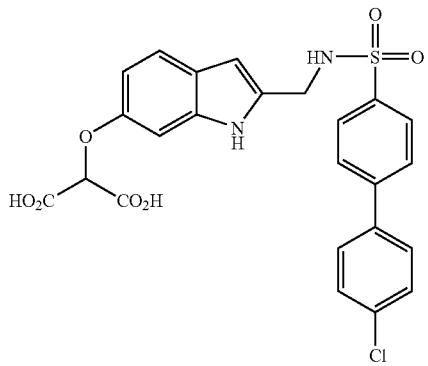

$^1$H NMR (400 MHz, DMSO-d6): δ 10.80 (s, 1H), 8.06 (t, 1H), 7.77-7.83 (m, 4H), 7.66 (d, 2H), 7.49 (d, 2H), 7.21 (d, 1H), 6.76 (s, 1H), 6.56 (m, 1H), 6.06 (s, 1H), 5.14 (s, 1H), 4.02 (d, 2H); MS (ES-) m/z 513 (M−1).

Example 34

2-(2-Benzylcarbamoyl-1H-indol-6-yloxy)-malonic acid

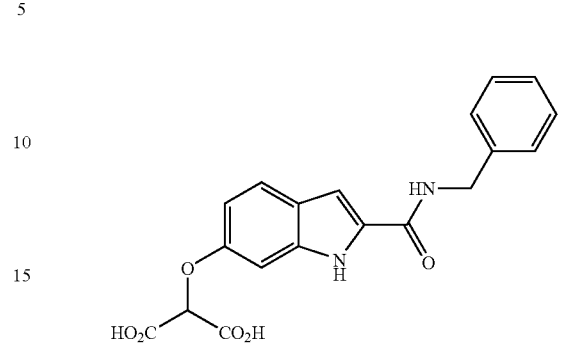

$^1$H NMR (400 MHz, DMSO-d6): δ 11.44 (s, 1H), 8.89 (t, 1H), 7.50 (d, 1H), 7.31 (m, 4H), 7.22 (m, 1H), 7.09 (d, 1H), 6.88 (d, 1H), 6.73 (m, 1H), 5.24 (s, 1H), 4.47 (d, 2H); MS (ES-) m/z 367 (M−1).

Example 35

2-(2-Phenethylcarbamoyl-1H-indol-6-yloxy)-malonic acid

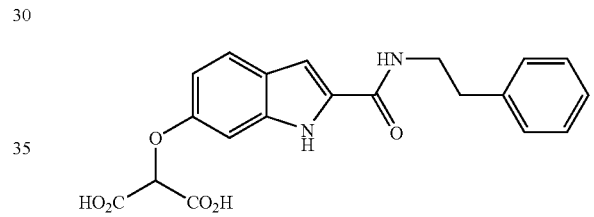

$^1$H NMR (400 MHz, DMSO-d6): δ0 11.39 (s, 1H), 8.43 (t, 1H), 7.50 (d, 1H), 7.15-7.29 (m, 5H), 7.00 (s, 1H), 6.86 (s, 1H), 6.73 (m, 1H), 5.24 (s, 1H), 3.49 (m, 2H), 2.85 (m, 2H); MS (ES-) m/z 381 (M−1).

Example 36

2-[2-(4-Phenyl-butylcarbamoyl]-1H-indol-5-yloxyl-malonic acid

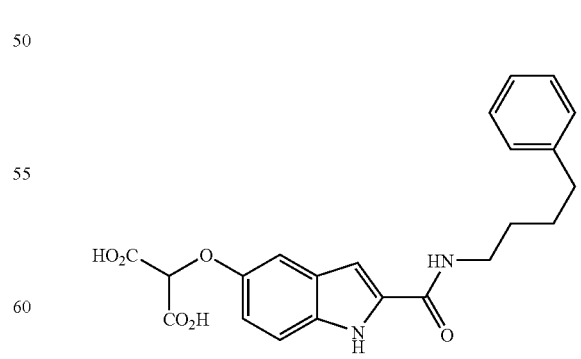

$^1$H NMR (400 MHz, DMSO-d6): δ 11.42 (s, 1H), 8.40 (t, 1H), 7.30 (d, 1H), 7.10-7.29 (m, 5H), 7.05 (s, 1H), 6.98 (s, 1H), 6.90 (s, 1H), 5.24 (s, 1H), 3.30 (m, 2H); 2.65 (m, 2H), 1.60 (m, 4H), MS (ES-) m/z 409 (M−1).

Example 37

2-{2-[(Benzyl-phenylmethanesulfonyl-amino)-methyl]-1H-indol-6-yloxy}-malonic acid

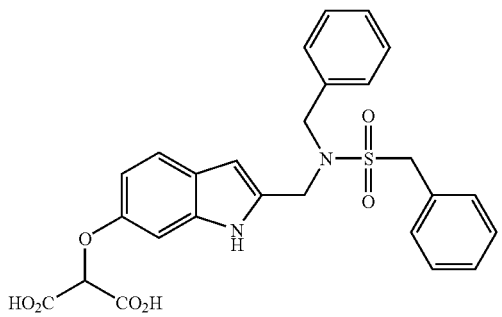

¹H NMR (400 MHz, DMSO-d6): δ 10.92 (s, 1H), 7.33 (d, 1H), 7.12-7.28 (m, 10H), 6.84 (s, 1H), 6.63 (m, 1H), 6.24 (s, 1H), 5.20 (s,1H), 4.28 (s, 2H); 4.23 (s, 2H), 4.15 (s, 2H), 2.65 (s, 3H); MS (ES-) m/z 507 (M−1).

Example 38

2-(2-{[(4-Phenyl-butyl)-phenylmethanesulfonyl-amino]-methyl}-1H-indol-6-yloxy)-malonic acid

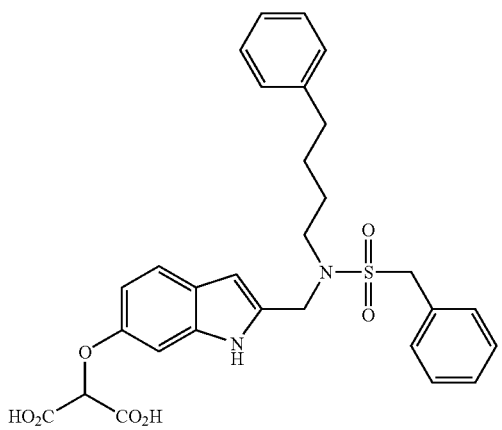

2-[2-(Phenylmethanesulfonylamino-methyl)-1H-indol-6-yloxy]-malonic acid diethyl ester (20 mg 0.042 mmol) of is dissolved in THF (1 ml). Ph₃P (17 mg, 0.063 mmol) and DIAD (128 mg, 0.063 mmol) are added. The mixture is stirred for 2 minutes and phenbutanol is added. The reaction is stirred overnight. The reaction mixture is concentrated and the residue is purified by column chromatography (15% ethyl acetate in hexanes) to obtain 14 mg of ester. The ester is dissolved in methanol (2 ml). 1N NaOH aqueous solution (0.40 ml) is added. The reaction is stirred for 1 hour and acidified with 1N HCl. The product was purified by C18 column (40% acetonitrile in water). ¹H NMR (400 MHz, DMSO-d6): δ 10.81 (s,1H), 7.29-7.36 (m, 6H), 7.18 (d, 2H), 7.12 (d, 1h), 7.03 (d, 2H), 6.874 (s, 1H), 6.65 (m, 1H), 6.28 (s, 1H), 5.16 (s, 1H), 4.36 (s, 2H); 4.31 (s, 2H), 3.04 (m, 2H), 2.39 (m, 2H), 1.20-1.35 (m, 4H); MS (ES-) m/z 549 (M−1).

Example 39

2-[3-Acetyl-2-(phenylmethanesulfonylamino-methyl)-1H-indol-6-yloxy]-malonic acid

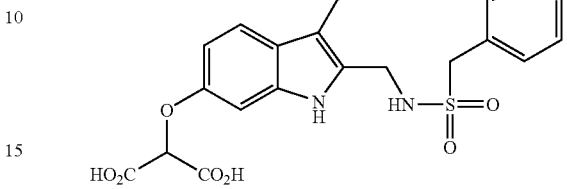

1H NMR (400 MHz, DMSO-d6): δ 11.67 (s, 1H), 7.74 (d, 2H), 7.58 (d, 2H), 7.35 (br s, 4 H), 6.76-6.85 (m, 3 H), 5.05 (s, 1H), 4.52 (d, 2H), 4.39 (br s, 2H), 2.50 (s, 3H); MS (ES-) m/z 415 (M-CO2H).

Example 40

2-[3-Benzoyl-2-(phenylmethanesulfonylamino-methyl)-1H-indol-6-yloxy]-malonic acid

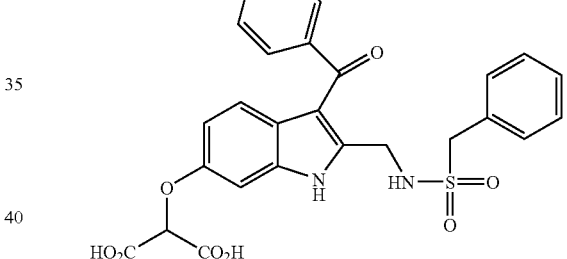

1H NMR (400 MHz, DMSO-d6): δ 11.83 (s, 1H), 7.61 (m, 3 H), 7.53 (m, 3H), 7.29 (m, 5H), 6.87-7.01 (m, 2H),. 6.66 (d, 1 H), 5.18 (s, 1H), 4.36 (d, 2H), 4.33 (s, 1H); MS (ES-) m/z 477 (M-CO2H).

Example 41

SHP-2 Assay Conditions

N-terminal 6 His-tagged, catalytic domain of SHP-2 (250-527) is expressed in *E. coli* and protein is purified by conventional methods. SHP-2's activity was assessed by measuring the fluorescent signal generated by the dephosphorylation of fluorescein diphosphate (FDP). The assay is carried out in 96-well polypropylene black plate. The final assay volume is 100 μL and comprises of 25 mM NaOAc, pH 6, 0.02% Triton X-100, 10 mM DTT and 2 nM SHP-2. Inhibitors are suspended in DMSO, and all reactions, including controls are performed at a final concentration of 3% DMSO. Reactions are initiated by the addition of 3 μM FDP and incubated at ambient temperature for 25 minutes. Plates were read using a Molecular Devices Gemini plate reader, Ex 485, Em 538, Cutoff 530.

The invention claimed is:
1. A compound having formula (I):

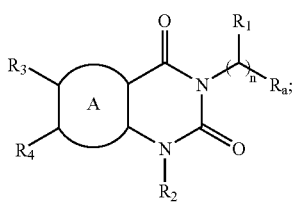

wherein:
ring A is an aryl ring wherein said aryl ring is either unsubstituted or substituted with one or more substituents selected from halogen, —R°, —OR°, —SR°, 1,2-methylene-dioxy, 1,2-ethylenedioxy; unsubstituted phenyl (Ph), unsubstituted —O(Ph), unsubstituted —CH$_2$(Ph), unsubstituted —CH$_2$CH$_2$(Ph) or (Ph), —O(Ph), —CH$_2$ (Ph), or —CH$_2$CH$_2$(Ph) substituted with one or more —R° groups; —NO$_2$, —CN, —N(R°)$_2$, —NR°C(O)R°, —NR°C(O)N(R°)$_2$, —NR°CO$_2$R°, —NR°NR°C(O) R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$ R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_q$NHC(O)R°; wherein:
q is 0-2; and wherein:
each R° is independently selected from hydrogen, a C$_{1-6}$ aliphatic, wherein said C$_{1-6}$ aliphatic group is either unsubstituted or substituted with one or more substituents selected from =O, =S, =NNHR*, =NN (R*)$_2$, =NNHC(O)R*, =NNHCO$_2$(alkyl), =NNHSO$_2$(alkyl), =NR*NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo C$_{1-4}$ aliphatic; an unsubstituted 5-6 membered heteroaryl or heterocyclic ring, phenyl, —O(Ph), or —H$_2$(Ph), or wherein two occurrences of R°, on the same substituent or different substituents, taken together, form a 5-8-membered heterocyclyl or heteroaryl ring having 1-3 heteroatoms independently selected from nitrogen, oxygen, or sulfur; wherein:
each R* is independently selected from hydrogen or a C$_{1-6}$ aliphatic group wherein said aliphatic group of R* is either unsubstituted or substituted with one or more substituents selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic);
the nitrogen of any non-aromatic heterocyclic ring is either unsubstituted or substituted with one or more groups selected from —R$^+$, —N(R$^+$)$_2$, —C(O)R$^+$, —OR$^+$, —CO$_2$R$^+$, —C(O)C(O)R$^+$, —C(O)CH$_2$C(O) R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein:
R$^+$ is hydrogen, an unsubstituted 5-6 membered heteroaryl or heterocyclic ring, an unsubstituted C$_{1-6}$ aliphatic, unsubstituted phenyl (Ph), unsubstituted —O(Ph), unsubstituted —CH$_2$(Ph), unsubstituted —CH$_2$CH$_2$(Ph); or C$_{1-6}$ aliphatic, phenyl (Ph), —O(Ph), —CH$_2$(Ph), or —CH$_2$CH$_2$(Ph) substituted with one or more groups selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic) or wherein two occurrences of R$^+$, on the same substituent or different substituents, taken together, form a 5-8-membered heterocyclyl or heteroaryl ring having 1-3 heteroatoms independently selected from nitrogen, oxygen, or sulfur;

R$_a$ is —COOH;
n is 1;
R$_1$ is a hydroxyaliphatic, aminoaliphatic, aliphatic-COOH, aliphatic-CONH$_2$, or arylaliphatic wherein said hydroxyaliphatic, aminoaliphatic, aliphatic-COOH, aliphatic-CONH$_2$, or arylaliphatic is either unsubstituted or substituted with one or more substituents selected from halogen, —R°, —OR°, —SR°, 1,2-methylene-dioxy, 1,2-ethylenedioxy; unsubstituted phenyl (Ph), unsubstituted —O(Ph), unsubstituted —CH$_2$(Ph), unsubstituted —CH$_2$CH$_2$(Ph) or (Ph), —O(Ph), —CH$_2$ (Ph), or —CH$_2$CH$_2$(Ph) substituted with one or more —R° groups; —NO$_2$, —CN, —N(R°)$_2$, —NR°C(O)R°, —NR°C(O)N(R°)$_2$, —NR°CO$_2$R°, —NR°NR°C(O) R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$ R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_q$NHC(O)R°; wherein:
q is 0-2; and wherein:
each R° is independently selected from hydrogen, a C$_{1-6}$ aliphatic, wherein said C$_{1-6}$ aliphatic group is either unsubstituted or substituted with one or more substituents selected from =O, =S, =NNHR*, =NN (R*)$_2$, =NNHC(O)R*, =NNHCO$_2$(alkyl), =NNHSO$_2$(alkyl), =NR*NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo C$_{1-4}$ aliphatic; an unsubstituted 5-6 membered heteroaryl or heterocyclic ring, phenyl, —O(Ph), or —CH$_2$(Ph), or wherein two occurrences of R°, on the same substituent or different substituents, taken together, form a 5-8-membered heterocyclyl or heteroaryl ring having 1-3 heteroatoms independently selected from nitrogen, oxygen, or sulfur; wherein:
each R* is independently selected from hydrogen or a C$_{1-6}$ aliphatic group wherein said aliphatic group of R* is either unsubstituted or substituted with one or more substituents selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic);
the nitrogen of any non-aromatic heterocyclic ring is either unsubstituted or substituted with one or more groups selected from —R$^+$, —N(R$^+$)$_2$, —C(O)R$^+$, —OR$^+$, —CO$_2$R$^+$, —C(O)C(O)R$^+$, —C(O)CH$_2$C(O) R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein:
R$^+$ is hydrogen, an unsubstituted 5-6 membered heteroaryl or heterocyclic ring, an unsubstituted C$_{1-6}$ aliphatic, unsubstituted phenyl (Ph), unsubstituted —O(Ph), unsubstituted —CH$_2$(Ph), unsubstituted —CH$_2$CH$_2$(Ph); or C$_{1-6}$ aliphatic, phenyl(Ph), —O(Ph), —CH$_2$(Ph), or —CH$_2$CH$_2$(Ph) substituted with one or more groups selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic) or wherein two occurrences of R$^+$, on the same substituent or different substituents, taken together, form a 5-8-membered heterocyclyl or heteroaryl ring having 1-3 heteroatoms independently selected from nitrogen, oxygen, or sulfur;

$R_2$ is an unsubstituted aliphatic, or a cycloaliphatic-aliphatic or heteroarylaliphatic, wherein said cycloaliphatic-aliphatic or heteroarylaliphatic is either unsubstituted or substituted with one or more substituents selected from halogen, —R°, —OR°, —SR°, 1,2-methylene-dioxy, 1,2-ethylenedioxy; unsubstituted phenyl (Ph), unsubstituted —O(Ph), unsubstituted —CH$_2$(Ph), unsubstituted —CH$_2$CH$_2$(Ph) or (Ph), —O(Ph), —CH$_2$(Ph), or —CH$_2$CH$_2$(Ph) substituted with one or more —R° groups; —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_q$NHC(O)R°;

wherein:

q is 0-2; and wherein:

each R° is independently selected from hydrogen, a $C_{1-6}$ aliphatic, wherein said $C_{1-6}$ aliphatic group is either unsubstituted or substituted with one or more substituents selected from =O, =S, =NNHR*, =NN(R*)$_2$, =NNHC(O)R*, =NNHCO$_2$(alkyl), =NNHSO$_2$(alkyl), =NR*NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo $C_{1-4}$ aliphatic; an unsubstituted 5-6 membered heteroaryl or heterocyclic ring, phenyl, —O(Ph), or —CH$_2$(Ph), or wherein two occurrences of R°, on the same substituent or different substituents, taken together, form a 5-8-membered heterocyclyl or heteroaryl ring having 1-3 heteroatoms independently selected from nitrogen, oxygen, or sulfur; wherein:

each R* is independently selected from hydrogen or a $C_{1-6}$ aliphatic group wherein said aliphatic group of R* is either unsubstituted or substituted with one or more substituents selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo($C_{1-4}$ aliphatic);

the nitrogen of any non-aromatic heterocyclic ring is either unsubstituted or substituted with one or more groups selected from —R$^+$, —N(R$^+$)$_2$, —C(O)R$^+$, —OR$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein:

R$^+$ is hydrogen, an unsubstituted 5-6 membered heteroaryl or heterocyclic ring, an unsubstituted $C_{1-6}$ aliphatic, unsubstituted phenyl (Ph), unsubstituted —O(Ph), unsubstituted —CH$_2$(Ph), unsubstituted —CH$_2$CH$_2$(Ph); or $C_{1-6}$ aliphatic, phenyl(Ph), —O(Ph), —CH$_2$(Ph), or —CH$_2$CH$_2$(Ph) substituted with one or more groups selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo ($C_{1-4}$ aliphatic) or wherein two occurrences of R$^+$, on the same substituent or different substituents, taken together, form a 5-8-membered heterocyclyl or heteroaryl ring having 1-3 heteroatoms independently selected from nitrogen, oxygen, or sulfur;

$R^3$ and $R^4$ are independently selected from $R^{11}$, $R^{12}$, $R^{14}$ or $R^{15}$;

wherein:

each $R^{11}$ is independently selected from 1,2-methylenedioxy, 1,2-ethylenedioxy, $R^6$ or (CH$_2$)$_m$—Y;

wherein m is 0, 1 or 2; and

Y is selected from halogen, CN, NO$_2$, CF$_3$, OCF$_3$, OH, SR$^6$, S(O)R$^6$, SO$_2$R$^6$, NH$_2$, NHR$^6$, N(R$^6$)$_2$, NR$^6$R$^8$, COOH, COOR$^6$ or OR$^6$;

each $R^{12}$ is independently selected from ($C_1$-$C_6$)-straight or branched alkyl, or ($C_2$-$C_6$)-straight or branched alkenyl or alkynyl; and each $R^{12}$ optionally comprises up to 2 substituents, wherein:

the first of said substituents, if present, is selected from $R^{11}$, $R^{14}$ and $R^{15}$, and the second of said substituents, if present, is $R^{11}$;

each $R^{14}$ is independently selected from OR$^{15}$, OC(O)R$^6$, OC(O)R$^{15}$, OC(O)OR$^6$, OC(O)OR$^{15}$, OC(O)N(R$^6$)$_2$, OP(O) (OR$^6$)$_2$, SR$^6$, SR$^{15}$, S(O)R$^6$, S(O)R$^{15}$, SO$_2$R$^6$, SO$_2$R$^{15}$, SO$_2$N(R$^6$)$_2$, SO$_2$NR$^{15}$R$^6$, SO$_3$R$^6$, C(O)R$^{15}$, C(O)OR$^{15}$, C(O)R$^6$, C(O)OR$^6$, NC(O)C(O)R$^6$, NC(O)C(O)R$^{15}$, NC(O)C(O)OR$^6$, NC(O)C(O)N(R$^6$)$_2$, C(O)N(R$^6$)$_2$, C(O)N(OR$^6$)R$^6$, C(O)N(OR$^6$)R$^{15}$, C(NOR$^6$)R$^6$, C(NOR$^6$)R$^{15}$, N(R$^6$)$_2$, NR$^6$C(O)R$^{11}$, NR$^6$C(O)R$^6$, NR$^6$C(O)R$^{15}$, NR$^6$C(O)OR$^6$, NR$^6$C(O)OR$^{15}$, NR$^6$C(O)N(R$^6$)$_2$, NR$^6$C(O)NR$^{15}$R$^6$, NR$^6$SO$_2$R$^6$, NR$^6$SO$_2$R$^{15}$, NR$^6$SO$_2$N(R$^6$)$_2$, NR$^6$SO$_2$NR$^{15}$R$^6$, N(OR$^6$)R$^6$, N(OR$^6$)R$^{15}$, P(O) (OR$^6$)N(R$^6$)$_2$, and P(O) (OR$^6$)$_2$;

each $R^{15}$ is a cycloaliphatic, aryl, heterocyclyl, or heteroaromatic; and each $R^{15}$ optionally comprises up to 3 substituents, each of which, if present, is $R^{11}$;

each $R^6$ is independently selected from H, ($C_1$-$C_6$)-straight or branched alkyl, or ($C_1$-$C_6$) straight or branched alkenyl; and each $R^6$ optionally comprises a substituent that is $R^7$;

$R^7$ is a cycloaliphatic, aryl, heterocyclyl, or heteroaromatic; and each $R^7$ optionally comprises up to 2 substituents independently chosen from H, ($C_1$-$C_6$)-straight or branched alkyl, ($C_2$-$C_6$) straight or branched alkenyl, 1,2-methylenedioxy, 1,2-ethylenedioxy, or (CH$_2$)$_p$-Z;

wherein p is 0, 1 or 2; and

Z is selected from halogen, CN, NO$_2$, CF$_3$, OCF$_3$, OH, S($C_1$-$C_6$)-alkyl, SO($C_1$-$C_6$)-alkyl, SO$_2$($C_1$-$C_6$)-alkyl, NH$_2$, NH($C_1$-$C_6$)-alkyl, N(($C_1$-$C_6$)-alkyl)$_2$, N(($C_1$-$C_6$)-alkyl)R$^8$, COOH, C(O)O($C_1$-$C_6$)-alkyl or O($C_1$-$C_6$)-alkyl; and R$^8$ is —C(O)CH$_3$, —C(O)Ph or —SO$_2$Ph; provided that:

$R^3$ and $R^4$ are not simultaneously hydrogen;

when $R^3$ is H, then $R^4$ is not chloro; and when $R^4$ is H, then $R^3$ is not —SCH$_3$ or —NH—O(O)CH$_3$.

2. The compound according to claim 1, wherein ring A is an optionally substituted 6 membered aryl.

3. The compound according to claim 2, wherein ring A is phenyl.

4. The compound according to claim 1, wherein $R_1$ is —(CH$_2$)$_q$—X, wherein q is 1-4, and X is OH, NH$_2$, COOH or CONH$_2$, (C1-C6)-alkyl, or benzyl.

5. The compound according to claim 4, wherein $R_1$ is hydroxymethyl, methyl, —CH$_2$COOH, —CH$_2$CONH$_2$, aminobutyl, or isopentyl.

6. The compound according to claim 1, wherein $R_2$ is selected from butyl, isobutyl, cyclopentyl, cyclohexylmethyl, pyridylmethyl, furanylmethyl, or thienylmethyl.

7. The compound according to claim 6, wherein $R_2$ is selected from 2-furanylmethyl.

8. The compound according to claim 1 wherein $R_3$ and $R_4$ are independently selected from hydrogen, halo, acetamido, allyloxy, thiophenyl, sulfoxyalkyl, or sulfoxyphenyl.
9. A compound selected from:
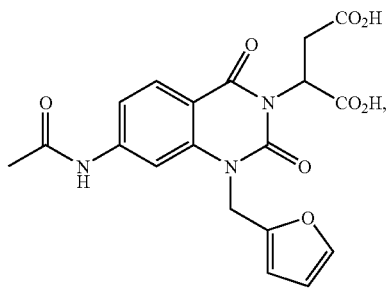
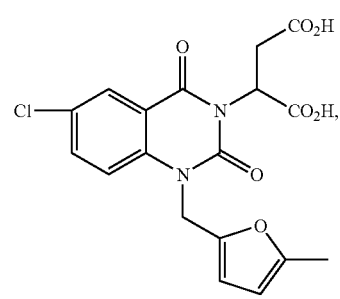
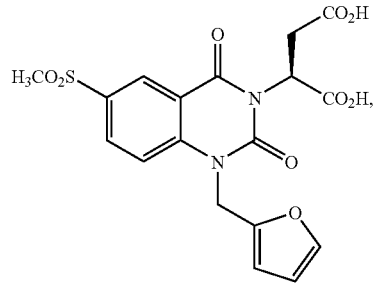
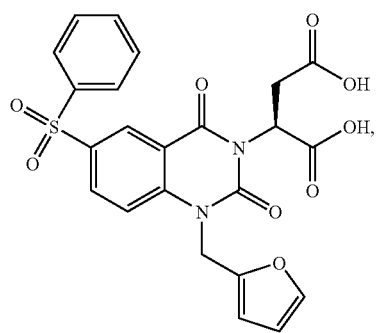
-continued
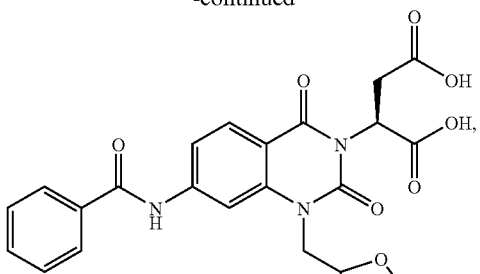
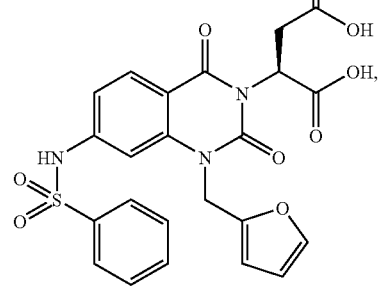
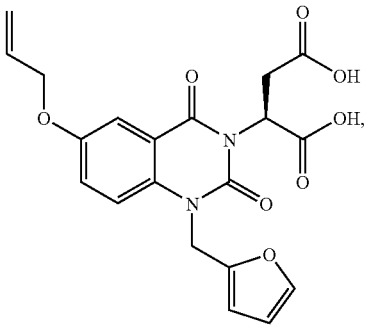
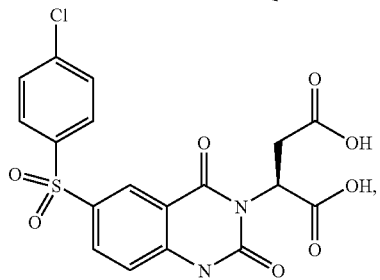
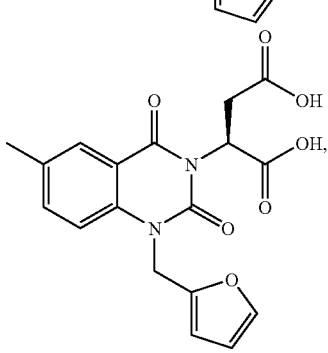

-continued
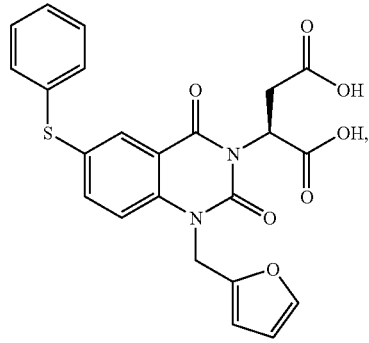
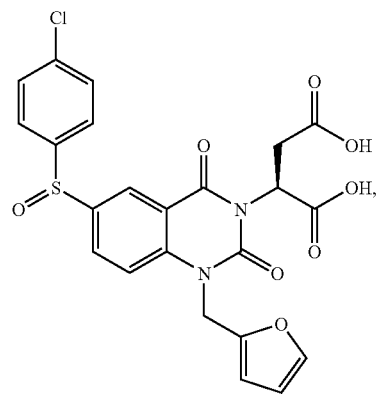
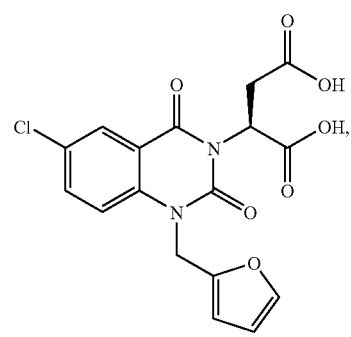
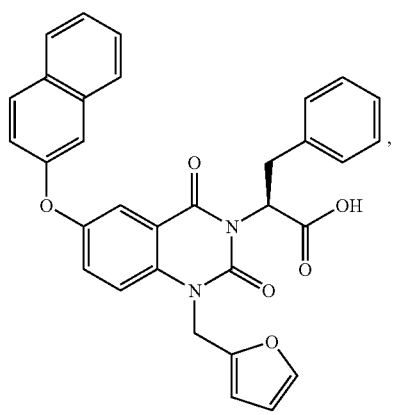
-continued
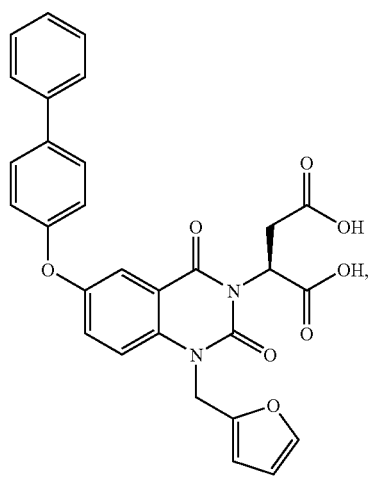
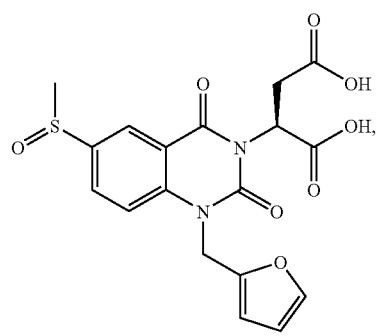
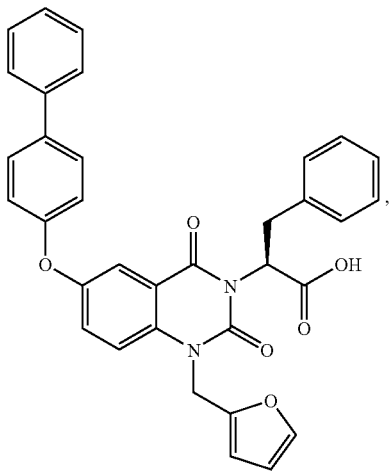

-continued
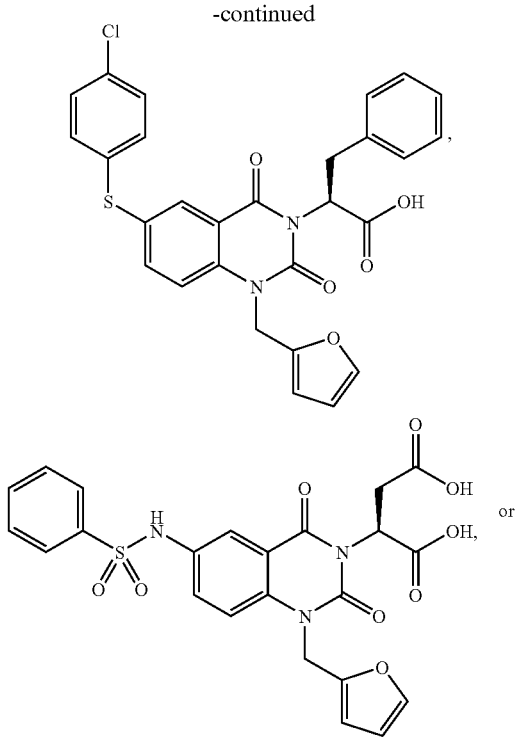
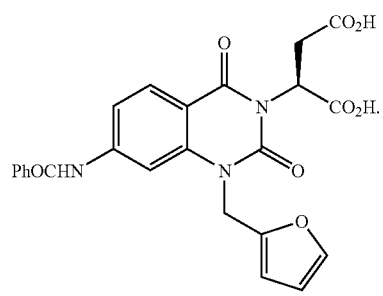
10. A pharmaceutical composition comprising a compound according to any one of claims 1-7 and 8-9 and a pharmaceutically acceptable adjuvant or carrier.
* * * * *